United States Patent
Dodinet et al.

(10) Patent No.: US 12,303,587 B2
(45) Date of Patent: May 20, 2025

(54) **EXTRACT OF *MORINGA peregrina* SEED CAKE, METHOD FOR OBTAINING SAME AND USE THEREOF IN COSMETIC OR NUTRICOSMETIC COMPOSITIONS**

(71) Applicant: AGENCE FRANCAISE POUR LE DEVELOPPEMENT D'AL ULA, Paris (FR)

(72) Inventors: Elizabeth Dodinet, Saint-Laurent d'Olt (FR); Vincent Bourgeteau, Ferel (FR)

(73) Assignee: AGENCE FRANCAISE POUR LE DEVELOPPEMENT D'AL ULA, Paris (FR)

( * ) Notice: Subject to any disclaimer, the term of this patent is extended or adjusted under 35 U.S.C. 154(b) by 0 days.

(21) Appl. No.: 17/633,350

(22) PCT Filed: May 21, 2021

(86) PCT No.: PCT/EP2021/063707
§ 371 (c)(1),
(2) Date: Feb. 7, 2022

(87) PCT Pub. No.: WO2021/234166
PCT Pub. Date: Nov. 25, 2021

(65) Prior Publication Data
US 2023/0070929 A1   Mar. 9, 2023

(30) Foreign Application Priority Data

May 21, 2020  (FR) ........................................ 2005433
Mar. 16, 2021 (FR) ........................................ 2102631

(51) Int. Cl.
| | | |
|---|---|---|
| A61K 8/9789 | (2017.01) |
| A61Q 19/00 | (2006.01) |
| A61Q 19/02 | (2006.01) |
| A61Q 19/08 | (2006.01) |

(52) U.S. Cl.
CPC .......... *A61K 8/9789* (2017.08); *A61Q 19/007* (2013.01); *A61Q 19/02* (2013.01); *A61Q 19/08* (2013.01); *A61K 2800/92* (2013.01)

(58) Field of Classification Search
None
See application file for complete search history.

(56) References Cited

U.S. PATENT DOCUMENTS

| 6,500,470 B1 | 12/2002 | Pauly |
|---|---|---|
| 2012/0128607 A1 | 5/2012 | Mandeau et al. |

FOREIGN PATENT DOCUMENTS

| CN | 102458355 | * | 5/2012 | | |
|---|---|---|---|---|---|
| CN | 106800586 A | | 6/2017 | | |
| CN | 107012190 A | | 8/2017 | | |
| CN | 108486202 A | | 9/2018 | | |
| CN | 103223000 A | | 7/2023 | | |
| EP | 3280272 A1 | * | 2/2018 | ............... | A23L 2/52 |
| FR | 2776519 A1 | | 10/1999 | | |
| JP | 04709377 B2 | | 6/2011 | | |
| JP | 2012-530769 A | | 12/2012 | | |
| JP | 2019-502731 A | | 1/2019 | | |
| WO | WO-2006029757 A1 | * | 3/2006 | ............. | A61K 8/645 |
| WO | 2019/138182 A1 | | 7/2019 | | |

OTHER PUBLICATIONS

Hm Abu-Tarboush et al. "Characterization of Hydrolysates Produced by Enzymatic hydrolysis of Camel Casein and Protein Isolates of Al-Ban (*Moringa peregrina*) and Karkade (*Hibiscus sabderiffa*) Seeds"; J. Saudi Socfor Agric. Sci., vol. 4, No. 2, Jan. 1, 2005 (Jan. 1, 2005), pp. 61-82; XP055753092.

Nashef As et al. "Effects of Alkali on Proteins. Disulfides and Their 1-9 Products"; Journal of Agricultural and Food Chemistry, American Chemical Society, Books and Journals Division, vol. 25, No. 2, Mar. 1, 1977, pp. 245-251; DOI: 10.1021/JF60210A020; ISSN: 0021-8561, XP001087830.

Rao Mb et al. "Molecular and biotechnological aspects of microbial proteases"; Microbiology and Molecular Biology Reviews, American Society for Microbiology, US, vol. 62, No. 3, Sep. 1, 1998 (Sep. 1, 1998), pp. 597-635; ISSN: 1092-2172, XP002245348.

T. Shantha Raju. "Proteolysis of Proteins"; In: Co? and Post-Translational Modifications of Therapeutic Antibodies and Proteins.; Hoboken. NJ. USA.: John Wiley & Sons. Inc. pp. 183-202. Apr. 2, 2019 (Apr. 2, 2019).; ISBN: 978-1-119-05331-6. XP055753173.

Young-Shick Hong et al. "Molecular Weight Distribution of Protein Hydrolysate by the Enzymic Hydrolysis of Weakly Acid-Treated Wheat Gluten"; Food Science and Technology Research, CH, vol. 7, No. 2, Jan. 1, 2001 (Jan. 1, 2001), pp. 126-130; DOI: 10.3136/fstr.7.126 ISSN: 1344-6606, XP055753367.

Zhou Xu et al. "Purification and identification immunomodulatory peptide from rice protein hydrolysates"; Food and Agricultural Immunology., GB, vol. 30, No. 1, Jan. 1, 2019 (Jan. 1, 2019), pp. 150-162 DOI: 10.1080/09540105.2018.1553938; ISSN: 0954-0105, XP055753384.

(Continued)

*Primary Examiner* — David J Blanchard
*Assistant Examiner* — Sarah J Chickos
(74) *Attorney, Agent, or Firm* — Tarolli, Sundheim, Covell & Tummino LLP

(57) ABSTRACT

The invention relates to an extract of *Moringa peregrina* seed cake predominantly comprising mainly a peptide hydrolyzate and to a process for obtaining the extract. The invention also relates to cosmetic or nutricosmetic compositions comprising said extract and to the use of said compositions for improving the appearance of the skin, mucous membranes or the integuments, for preventing and/or combating dryness of the skin and mucous membranes, for preventing and/or combating the signs of aging and/or photoaging of the skin, for promoting skin bleaching and for promoting slimming.

10 Claims, 1 Drawing Sheet

(56) References Cited

OTHER PUBLICATIONS

Mendel Friedman et al. "Protein-Alkali Reactions: Chemistry, Toxicology, and Nutritional Consequences", Jan. 1, 1984 (Jan. 1, 1984), Retinal Degenerative Diseases, Springer, US,pp. 367-412, Retrieved from the Internet: https://link.springer.com/chapter/I 0.1007 /978-1-46 84-4790-3_18; . XP009524239.
Kjaer A et al. "Isothiocyanates in Myrosinase-Treated Seed Extracts of Moringa Peregrina"; Phytochemistry, Elsevier, Amsterdam, NL, vol. 18, No. 9, Jan. 1, 1979 (Jan. 1, 1979), pp. 1485-1487; DOI: 10.10 I 6/S003 I-9422(00)98480-2; ISSN: 0031-9422, XP009024211.
Afsharypuora S et al. "Volatile constituents of the seed kernel and leaf of Moringa peregrina (forssk.) Fiori, Agricolt. cultivated in Chabahar (IRAN)" RAN/AN Journal of Pharmaceutical Sciences, Iranian Society of Pharmaceutical Scientists, Jr, vol. 6, No. 2, Jan. 1, 2010 (Jan. 1, 2010), pp. 141-144; ISSN: 1735-2444, XP009508062.
Al-Dabbas Maher Met al. "Chemical composition and oil components in seeds of Moringa peregrina (Forssk) Fiori" Crop Research, Agricultural Research Information Centre, Hisar, IN, vol. 40, Jan. 1, 2010 (Jan. 1, 2010), pp. 161-167 ISSN: 0970-4884, XP009163458.
International Application No. PCT/EP2021/063707 Filed May 21, 2021; International Search Report; Authorized Officer: Jesko Bars; Jul. 6, 2021; 10 pp.
Chinese Office Action dated Aug. 19, 2022.
Indian Office Action dated Jan. 6, 2023.
Key Attributes of TKDL AB/851.
Key Attributes of TKDL AB/847.
https://www.moyoway.com/naturalbeauty.html.
Https://www.allure.com/story/what-ismoringa-oil-skin-care-ingredient.
Skoczynska, Anna, et al., "Melanin and lipofuscin as hallmarks of skin aging", Advances in Dermatology and Allergology 2, Apr. 2017, pp. 97-103.

* cited by examiner

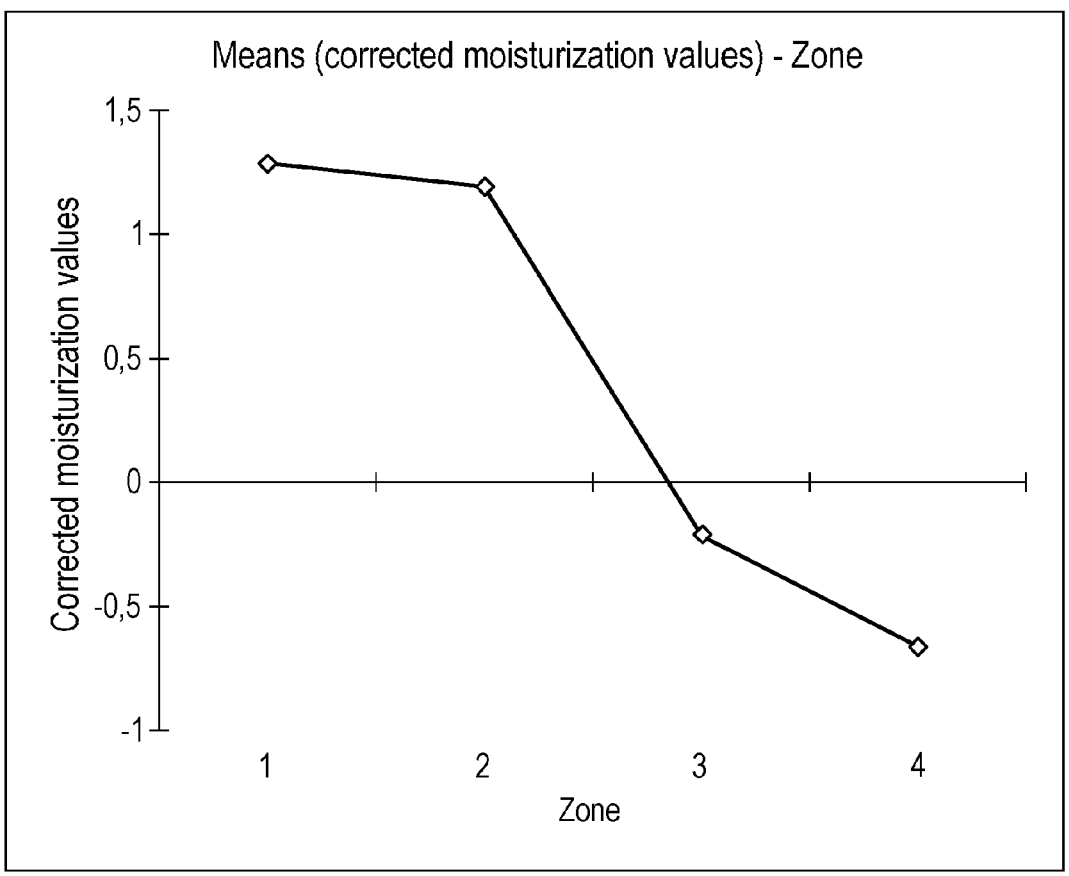

EXTRACT OF *MORINGA peregrina* SEED CAKE, METHOD FOR OBTAINING SAME AND USE THEREOF IN COSMETIC OR NUTRICOSMETIC COMPOSITIONS

TECHNICAL FIELD

The invention relates to the cosmetic and nutricosmetic field and more particularly to the field of active ingredients included in the formulation of skincare compositions. The invention relates to an extract of *Moringa peregrina* seed cake predominantly comprising a peptide hydrolyzate. The invention also relates to the process for obtaining the particular extract of *Moringa peregrina* seed cake, to cosmetic or nutricosmetic compositions comprising such extracts and, finally, to the cosmetic or nutricosmetic use of such compositions for caring for the skin, the scalp and the integuments.

TECHNICAL BACKGROUND

The Moringaceae are a mono-generic family (only one genus, *Moringa adans*), an element of the Saharo-Sindian flora, constituted of between 12 and 14 species according to the authors, distributed from Eastern Africa to Asia. The genus is conventionally divided into three sections which are, however, not confirmed as monophyletic by the phylogenetic analyses. Said analyses have rather revealed clades centered on certain morphological characters: pachycauls ("bottle trees"); "tuberous trees" and those that are neither bottle trees nor tuberous trees ("slender trees"). The species *Moringa peregrina* (Forssk.) Fiori, belongs to the third group. The sparse genetic studies on the genus or the family confirm the reality of the species relative to the other species in the genus, notably with respect to Indian *Moringa*, *Moringa oleifera* Lam. (see notably the articles: OLSON, M. E. 2002, Combining Data from DNA Sequences and Morphology for a Phylogeny of Moringaceae (Brassicales), *Systematic Botany* 27(1): 55-73; HASSANEIN, A. M. A. AND AL-SOQEE, A. A., 2018, Morphological and genetic diversity of *Moringa oleifera* and *Moringa peregrina* genotypes, *Horticulture, Environment and Biotechnology* 59(2): 251-261). A recent article on *Moringa peregrina* sampled on various locations in Saudi Arabia concluded, by using ITS markers, that there was genetic stability of the species (ALAKLABI, A., 2015, Genetic diversity of *Moringa peregrina* species in Saudi Arabia with ITS sequences, *Saudi Journal of Biological Sciences* 22: 186-190) with, however, a high level of intra-population genetic variation.

The species *Moringa peregrina* is found in the rocky environments of Yemen, Oman, Saudi Arabia, Eastern Africa, Sudan, Ethiopia, Eritrea, Somalia and Djibouti. Its presence in Iran appears limited to the south-eastern provinces, but this requires confirmation (PROTA14=MUNYANZIZA E. AND YONGABI K. A., Vegetable oils/Oleaginous plants, *Moringa peregrina* (Forssk.) Fiori, http://database.prota.org/protahtml/*moringa peregrina*_fr.htm, accessed on 10/23/2019). In the Middle East and in Egypt, the species is now only represented by rare dispersed relicit stations (with the exception of a few populations at altitude), mainly in the sectors of the Sudan area. *Moringa peregrina* is today also considered as being rare and in danger in Sudan and Yemen. Relative to the other species of its clad, *Moringa peregrina* occupies the most arid and inhospitable habitats. It is apparently more drought-resistant than *Moringa oleifera* which is planted commercially on a large scale in the tropical and subtropical zones.

Recent studies have shown that the size and girth of the seeds had a favorable impact on the germination time and the rate and speed of growth of the young individuals (GOMAA N. H. AND PICÓ F. X., 2011, Seed germination, seedling traits, and seed bank of the tree *Moringa peregrina* (Moringaceae) in a hyper-arid environment, *American Journal of Botany* 98(6): 1024-1030), indicating an adjustment in the allocation of resources regarding the seed quality rather than the number, which enables *Moringa peregrina* to reproduce efficiently in extreme (hyper-arid) abiotic environments. *Moringa peregrina* seeds have a thicker central mesotesta, in terms of cell layer, than those of *Moringa oleifera*.

A few historical reports exist which tend to indicate that *Moringa peregrina* oil was actively traded at the dawn of Islam in the region of Al-Ula (NASEEF, A. A. S., 1995, Al-'Ulā, *A study of Cultural and Social Heritage*). The oil produced from *Moringa peregrina* is nowadays mainly destined for personal consumption or for local markets. In Saudi Arabia, the leaves were traditionally used as a decoction for internal use for treating diabetes, bowel diseases, ocular diseases and anemias (ABDEL-KADER, M. S., HAZAZI A. M. A., ELMAKKI O. A. AND ALQASOUMI S. I., 2018, A survey on the traditional plants used in Al Kobah village, *Saudi Pharmaceutical Journal* 26(6): 817-821) and as a diuretic, rubefacient and astringent (AQEEL A. A. M., TARIQ M., MossA J. S., AL-YAHYA M. A. AND AL-SAID M. S., 1984, "Plants used in Arabian Folk medicine", *Report submitted to Saudi Arabian National Centre for Science and Technology*, Riyadh, Saudi Arabia). In Oman, the oil, extracted by women at the end of the summer, is used to combat migraine, fever, burns, lacerations and fractures, constipation and stomach pains, and to combat muscular pain and dryness of the hair (GHAZANFAR S. A., 1994, *Handbook of Arabian Medicinal Plants*, 1$^{st}$ ed., CRC Press, Boca Raton, Ann Arbor, U.S.; GHAZANFAR S. A., 1998, Plants of Economic Importance, cap. 15, in GHAZANFAR, S. A. AND FISHER, M. (ed.) *Vegetation of the Arabian Peninsula*. Geobotany 25, pages 241-264, Kluwer Academic Publishers, table 11.1, page 247 and 11.7 page 251).

It was also used in fragranced compositions (GHAZANFAR S. A., 1998, page 259) and in Oman and Yemen as a face lotion (GHAZANFAR S. A. AND RECHINGER B., 1996, Two multi-purpose seed oils from Oman. *Plants for Food and Medicine. Paper presented at the joint meeting of the Society for Economic Botany and International Society for Ethnopharmacology*, Jul. 1-7, 1996, London).

Extracts originating from *Moringa oleifera* seeds are known in the cosmetic field. For example, FR 296 879 discloses an extract of whole seeds (with teguments) of *Moringa oleifera* containing, per 100 g of dry extract, from 5% to 50% of oil (including triglycerides, fatty acids and polar lipids) and from 0.01% to 5% of polyphenols, and the use thereof in cosmetic compositions for combating aging of the skin. In said document, extraction with a moderately polar solvent is performed on the whole seed of *Moringa oleifera*.

It is also known from FR 2 776 519 that protein extracts from *Moringa oleifera* seeds, which are known for their clarifying effects on turbid waters, have a softening, physiological conditioning, moisturizing, restructuring and repairing effect and an antipollution effect on the skin and mucous membranes. In said document, the active principles are proteins with molecular weights of between 6500 and 8800 Da, which are obtained by aqueous extraction of *Moringa oleifera* cake with 4N sodium hydroxide for one hour at pH 7.5.

It is also known from FR 2 825 267 that extracts of whole or ground, shelled or unshelled *Moringa* seeds, or seeds on which milling has been performed or defatted or non-defatted protein extracts, have benefits in the fields of deodorization and the suppression of unpleasant odors, cleanliness, intimate hygiene, oral hygiene and dental care, and also softening, moisturizing, calmative and antifatigue cosmetic properties on the skin. In said document, it is demonstrated that the whole protein extracts have increased activity when the seed is not de-oiled.

FR 3 076 460 relates to the use of a protein extract of non-germinated and de-oiled *Moringa oleifera* seeds for treating sensitive, sensitized, reactive, fragile and/or embrittled skin and/or mucous membranes and/or in the treatment and/or prevention of erythema, in particular diaper rash of infants. In said document, the extraction process enables the production of a major fraction of proteins with molecular weights of about 8800 Da.

Finally, KR2013/0088224 discloses the use of an extract of germinated whole *Moringa oleifera* seeds in cosmetics, in particular obtained by extraction using a supercritical fluid. Said process makes it possible to isolate apolar amino acids and carotenoids, which are described as active agents for bleaching cosmetic use.

All the abovementioned documents relate to the use of the species *Moringa oleifera*; none of them describes the use in the cosmetic field of extracts obtained from the species *Moringa peregrina*.

More specifically, for the species *Moringa peregrina*, it is known that certain phenolic and flavonoid compounds obtained from the leaves or whole seed of *Moringa peregrina* have antioxidant activity (AL-DABBAs M., 2017, Antioxidant activity of different extracts from the aerial part of *Moringa peregrina* (Forssk.) Fiori, from Jordan, *Pakistan Journal of Pharmaceutical Sciences*, 30(6): 2151-2157). These compounds are extracted with solvents such as methanol, ethyl acetate or hexane from the leaves or the whole seeds. It appears that it is the leaves which comprise the largest amount of active compounds. XP055753092, 2005 from ABU TARBOUSH et al. also discloses the extraction of a hydrolyzate from shelled *Moringa peregrina* seeds produced by enzymatic hydrolysis over a period of 10 hours. The aim of this extraction is to obtain a product which has a high capacity for absorbing oil and water. Finally, NASHEF et al., XP0010830, 1977, discloses in general the consequences of alkaline hydrolysis mainly on pure proteins which may lead to modifications of the physical and chemical properties of the proteins and also of their nutritive value. The hydrolysis conditions used with 0.1 M sodium hydroxide are a temperature of 50° C. for a period of 24 hours. Said document mentions renal lesions in rats fed with proteins treated with bases under these conditions.

Thus, depending on the species used in the genus *Moringa*, it is observed that, depending on the plant part (leaf or seed), the seed part (whole seed or otherwise, shelled or unshelled) and the extraction process performed, notably the choice of solvent, the molecules extracted prove to be different. Now, the composition of the extract conditions the biological activity and consequently the cosmetic efficacy.

Given the foregoing, one problem that the invention proposes to solve is that of developing novel products based on an extract of the species *Moringa peregrina* of the genus *Moringa* and of the family Moringaceae that may be used in cosmetics and that are easy to use.

Accordingly, the Applicant has revealed a novel extract obtained from the cake of seeds of the species *Moringa peregrina*, which improves the appearance of the skin, mucous membranes and the integuments and notably for preventing and/or combating dryness of the skin and/or the mucous membranes, for preventing and/or combating the signs of aging and/or photoaging of the skin, for promoting skin bleaching and preventing age marks, and also for promoting slimming and preventing or relieving skin redness. The extract according to the invention predominantly comprises a peptide hydrolyzate of *Moringa peregrina* seed cake. The extract specifically obtained from the cake of unshelled *Moringa peregrina* seeds is novel in two respects in the cosmetic field relative to the extracts of the prior art, firstly owing to the specific species of origin used and secondly owing to its particular molecular profile.

By the intergovernmental agreement of Apr. 10, 2018 between the government of the French Republic and the Kingdom of Saudi Arabia, the Applicant, Agence Française Pour Le Développement d'AlUla (AFALULA) and the Commission Royale pour AlUlA (RCU) notably have the joint project of developing sustainable agriculture and the local economy, notably for the local production of natural products derived from indigenous plants and of protecting the biodiversity and the rights of the AlUla region of the Kingdom of Saudi Arabia. The Kingdom of Saudi Arabia is a member of the Nagoya Protocol since Oct. 8, 2020. At the time of drafting of the present patent, the implementing regulations in respect of which the Nagoya Protocol will be integrated into the relevant aspects of local law is under examination. Consequently, at this stage, the Kingdom of Saudi Arabia has no specific requirements as regards the present patent application and the Nagoya Protocol. Thus, at the date of filing of the patent application, there are no certificate of compliance requirements regarding access to genetic resources.

SUMMARY

A first subject of the invention is an extract of *Moringa peregrina* seed cake predominantly comprising a peptide hydrolyzate which comprises amino acid derivatives, amino acids, peptides and glycopeptides with a molecular weight of between 100 Da and 6000 Da, preferentially between 1500 Da and 5000 Da, more preferentially between 3000 Da and 4500 Da, and in that it is obtained from the unshelled seeds, when the fruit of *Moringa peregrina* is ripe, by chemical proteolysis at a pH of greater than 13 for a time of about 2 hours at a temperature of between 16 and 25° C.

By virtue of its particular features, the extract according to the invention is unique in the genus *Moringa* and in the family Moringaceae. It will be demonstrated that the extract of the species *Moringa peregrina* has a particular peptide hydrolyzate which is different from those known from the other species of the genus, notably from the species *Moringa oleifera*, which the Applicant has managed to reveal.

A second subject of the invention is a process for obtaining an extract of *Moringa peregrina* seed cake according to the invention, characterized in that it comprises the following steps in which:

a) the unshelled seeds, harvested when the fruit of *Moringa peregrina* is ripe, are collected and dried to obtain an internal moisture content of less than 8%, b) the dried seeds are pressed so as to separate the oil from the rest of the seed, so as to obtain the cake comprising less than 6% by weight of residual oil, c) the cake obtained in step b) is milled, d) the milled cake obtained in step c) is dispersed in aqueous phase, e) chemical proteolysis of the aqueous dispersion obtained in step d) is performed for a time of about 2 hours, at a pH of greater than 13 and at a temperature of between 16 and 25° C., f) the proteolysis is neutralized to stabilize the peptide hydrolyzate obtained, g) the peptide hydrolyzate is recovered by solid/liquid separation, h) the peptide hydrolyzate is purified by ultrafiltration and then, optionally, i) lyophilization of the peptide hydrolysate obtained in step h) is performed.

A third subject of the invention is a cosmetic or nutricosmetic composition comprising, as active agent, an effective amount of an extract of *Moringa peregrina* seed cake according to the invention and a physiologically acceptable excipient.

Lastly, a fourth subject of the invention is the cosmetic or nutricosmetic use of a composition according to the invention, for improving the appearance of the skin, mucous membranes or the integuments, for preventing and/or combating dryness of the skin and the mucous membranes, for preventing and/or combating the signs of aging and/or photoaging of the skin, for promoting bleaching of the skin and for promoting slimming.

BRIEF DESCRIPTION OF THE FIGURES

The invention will be better understood and further aims, details, features and advantages thereof will appear more clearly from the following description of several particular embodiments of the invention, given merely for illustration and without limitation, with reference to the attached drawings.

FIG. 1 represents the comparative results of the moisturizing effect of various products on the surface of the skin.

DESCRIPTION OF THE EMBODIMENTS

In this description, unless otherwise specified, it is understood that when a range is given, it includes the upper and lower limits of said range.

In the present invention, the following abbreviations have the meanings given below:

MTT: 3-(4,5-dimethylthiazol-2-yl)-2,5-diphenyltetrazolium bromide (the MTT test is a rapid method for counting live cells)

SDS: Sodium Dodecyl Sulfate

PBS: Phosphate-Buffered Saline

ELISA: Enzyme-Linked Immunosorbent Assay

PCR: Polymerase Chain Reaction

ANOVA: Analysis Of Variance

MSH: Melanocyte Stimulating Hormone

In the present invention, the following definitions apply:

"predominantly a peptide hydrolysate": an amount of greater than 10%, preferentially greater than 20%, more preferentially greater than 30% and which may be up to about 40% (mass/mass) of dry matter of peptides, oligopeptides, glycopeptides and amino acids or volatile nitrile derivatives thereof, more preferentially 50% of the weight of the dry matter.

"effective amount": the necessary amount of active molecules to obtain the desired result, namely making it possible notably to improve the appearance of the skin.

"proteolysis": the segmentation of proteins into peptides, oligopeptides and the basic fragments thereof (amino acids) via chemical or enzymatic hydrolysis.

"topical application": applying or spreading the active principle according to the invention, or a composition containing same, onto the surface of the skin, a mucous membrane or the integuments.

"physiologically acceptable": suitable for topical use, in contact with human skin, or for use via other routes of administration, for example orally or by injection into the skin, without any risk of toxicity, incompatibility, instability or allergic response.

"cake": the de-oiled part of the seed after pressing. It is the solid residue from the extraction of the oil from the seeds. It is a co-product of the grinding operation, the process for manufacturing the oil. It generally represents from 50% to 75% of the mass of the seeds.

"unshelled seeds": means that the shell (pericarp) and the tegument of the harvested seeds are kept around the kernels.

"when the fruit is ripe": means that the fruit is ripe, preferentially when the pod is at the start of dehiscence and turns a dark beige to brown color and when a 180° twist of the lower quarter of the pod brings about opening of the valves.

"about": a margin of plus or minus 10% to 20% relative to the given information.

"pool of active molecules", also "active principle": the peptide hydrolyzate extracted according to the process of the invention from the *Moringa peregrina* seed cake. This hydrolyzate is responsible for the biological activities described in the present invention.

"active agent": a sufficient amount of an extract according to the invention to obtain the biological activities described. Depending on whether the extract is liquid or dried, and concentrated or otherwise, the amounts of the active agent may vary in proportions of from 0.002% to 40% by weight relative to the total weight of the composition.

"signs of aging of the skin": any modification in the outer appearance of the skin and the integuments due to aging, for instance wrinkles and fine lines, wizened skin, sagging skin, thinning skin, lack of elasticity and/or tone of the skin, dull, lackluster skin or pigmentation spots on the skin, hair discoloring or nail stains, but also any internal modification of the skin that is not systematically reflected by a modified outer appearance, for instance any internal degradation of the skin following exposure to ultraviolet (UV) radiation.

A first subject of the invention is an extract of *Moringa peregrina* seed cake predominantly comprising a peptide hydrolyzate which comprises amino acid derivatives, amino acids, peptides and glycopeptides with a molecular weight of between 100 Da and 6000 Da, preferentially between 1500 Da and 5000 Da, more preferentially between 3000 Da and 4500 Da, and in that it is obtained from the unshelled seeds, when the fruit of *Moringa peregrina* is ripe, by chemical proteolysis at a pH of greater than 13 for a time of about 2 hours at a temperature of between 16 and 25° C.

The peptide hydrolyzate, comprising peptides, oligopeptides, glycopeptides and amino acids, as in the profile defined below, has never been demonstrated in an extract of seeds of the genus *Moringa peregrina*. The species *Moringa peregrina* grows in very arid climates. Thus, its ability to adapt to drought and to reproduce under extremophilic conditions has allowed it to acquire unique features, which the Applicant has been able to identify via the use of a specific extraction process on the *Moringa peregrina* seed cake.

In the context of the present invention, the plant part chosen is the cake of *Moringa peregrina* seeds. It is known that *Moringa peregrina* seeds are used for the extraction of their oil, which is useful for personal consumption or in various traditional medicinal treatments. The cake obtained after the seed has been de-oiled is a waste product that is currently notably used for animal feed.

According to a preferred embodiment, the extract according to the invention is obtained from the cake of unshelled *Moringa peregrina* seeds.

According to one embodiment, the peptide hydrolyzate of the extract according to the invention comprises amino acid derivatives, amino acids, peptides and glycopeptides with a molecular weight of between 100 Da and 6000 Da, more particularly between 1500 Da and 5000 Da and even more particularly between 3000 Da and 4500 Da.

According to another embodiment, the extract also comprises between 0.3% and 3% of volatile compounds, of which 50% of these compounds, i.e. between 0.15% and 1.5% of the extract according to the invention, is constituted of light nitrile compounds, mainly isobutyronitrile and methylbutanenitrile; of which 5% to 10% of these compounds, i.e. between 0.015% and 0.3% of the extract according to the invention, is constituted of isothiocyanate derivatives, mainly isopropyl isothiocyanate and isobutyl isothiocyanate; of which 1% to 5% of these compounds, i.e. between 0.003% and 0.15% of the extract according to the invention, is constituted of essential oil, mainly of eucalyptol, menthol and benzaldehyde.

A second subject of the invention is a process for obtaining an extract of *Moringa peregrina* seed cake according to the invention, comprising the following steps in which:
 a) the unshelled seeds, harvested when the fruit of *Moringa peregrina* is ripe, are collected and dried to obtain an internal moisture content of less than 8%,
 b) the dried seeds are pressed so as to separate the oil from the rest of the seed, so as to obtain the cake comprising less than 6% by weight of residual oil,
 c) the cake obtained in step b) is milled,
 d) the milled cake obtained in step c) is dispersed in aqueous phase,
 e) chemical proteolysis of the aqueous dispersion obtained in step d) is performed for a time of about 2 hours, at a pH of greater than 13 and at a temperature of between 16 and 25° C.,
 f) the proteolysis is neutralized to stabilize the peptide hydrolyzate obtained,
 g) the peptide hydrolyzate is recovered by solid/liquid separation,
 h) the peptide hydrolyzate is purified by ultrafiltration and then, optionally,
 i) lyophilization of the peptide hydrolysate obtained in step h) is performed.

The unshelled seeds are collected, i.e. the shell (pericarp) of which seeds is kept, when the fruit is ripe and preferentially when the pod is at the start of dehiscence.

The seeds are dried to obtain an internal moisture content of less than 8% and preferentially about 6%; drying is preferably performed on a ventilated rack sheltered from sunlight, preferably under shade in the open air.

The dried seeds are then milled extemporaneously with being cold pressed, which allows the oil to be mechanically separated from the rest of the compressed seed, i.e. the cake.

The cake is then mechanically milled with any type of mechanical mill such as a hammer mill, flail mill, knife mill, crushing/shredding mill, ball mill or pestle mill, but also with any type of cryomill.

The dispersion in aqueous phase according to step d) and the proteolysis according to step e) are advantageously always performed with stirring, thus allowing dispersion and homogenization of the solid in the liquid, thus improving the overall exchange surface and consequently the proteolysis.

A liquid peptide hydrolyzate with a density greater than 1 and preferentially of about 1.1 is obtained, comprising a dry matter content of between 10% and 15%, preferably about 12.5%, comprising between 1% and 6% of nitrogenous compounds, notably volatile nitrile derivatives in a proportion of from 0.5% to 1.5%, preferentially about 0.8%, and 20 mg/liter of polyphenols (0.0002%).

According to a preferential embodiment of the process according to the invention, the solid/liquid separation of step g) is performed by various processes such as centrifugation, dewatering or filtration.

According to another preferential embodiment of the process according to the invention, the ultrafiltration in step h) is performed with a cutoff threshold between 100 Da and 6000 Da, more particularly between 1500 Da and 5000 Da and even more particularly between 3000 Da and 4500 Da.

In one embodiment according to the invention, the process for obtaining a seed cake extract is obtained from the unshelled seed cake by proteolysis, with stirring, in a proportion of not more than 25% by weight of solid matter relative to the total weight used in the aqueous solvent, at a temperature of between 16 and 25° C. for a period of about 2 hours.

In one embodiment of the process for obtaining the liquid *Moringa peregrina* extract obtained, the peptide hydrolyzate is purified by distillation, microfiltration, ultrafiltration and/or nanofiltration to concentrate the extract as compounds of interest relative to the volatile nitrile derivatives also extracted. These purification steps make it possible to concentrate the pool of compounds of interest at the expense of other extracted compounds such as those mentioned.

In another embodiment of the extraction process according to the invention, the liquid extract obtained is dried so as to obtain a dry extract of the *Moringa peregrina* seed cake containing an amount of greater than 10%, preferentially greater than 20%, more preferentially greater than 30% and which may be up to about 40% (mass/mass) of dry matter of peptides, oligopeptides, glycopeptides and amino acids or the volatile nitrile derivatives thereof, more preferentially 50% of the weight of the dry matter.

According to one embodiment of the invention, the liquid *Moringa peregrina* seed cake extract obtained is preferentially dried, for example, by atomization, lyophilization or zeodration so as to obtain a solid *Moringa peregrina* seed extract, the water having been evaporated off. The drying may be performed in the presence of a drying support additive such as maltodextrin, cyclodextrin or inulin, or in the presence of a mineral support such as phyllosilicate, magnesium silicate or carbonate and salts thereof.

The invention also relates to the extract of the *Moringa peregrina* seed cake which may be obtained via the extraction process according to the invention.

A third subject of the invention is a cosmetic or nutricosmetic composition comprising, as active agent, an effective amount of an extract of *Moringa peregrina* seed cake according to the invention and a physiologically acceptable excipient.

The composition according to the invention may be formulated in the form of various preparations suitable for topical administration or for oral administration.

According to a first variant, the various preparations are suitable for topical administration and include creams, oil-in-water and water-in-oil emulsions, milks, ointments, lotions, oils, balms, aqueous or aqueous-alcoholic or glycolic solutions, sera, powders, patches, sprays or any other product for external application, for instance medical devices or cosmetic-textile products.

According to a second variant, the various preparations are suitable for oral administration; the plant extract comprising the peptide hydrolyzate which may be included either in a food composition or in a food supplement. The food supplement may be in the form of hard gel capsules or soft gelatin or vegetable capsules in the context of the present invention. Said food supplement may then contain from 0.01% to 100% by weight of the plant extract.

In the context of a food use, for nutritive or cosmetic (cosmeto-food or nutricosmetic) purposes, the composition will advantageously be formulated in the form of a preparation that is suitable for oral administration. It may comprise no excipient and may be constituted, in its entirety, of the plant extract comprising the peptide hydrolyzate in dried form.

According to a preferential embodiment, the compositions according to the invention are more particularly intended for topical administration. These compositions must thus contain a cosmetically acceptable medium, i.e. a medium that is compatible with the skin and the integuments, and cover all cosmetic forms. These compositions may notably be in the form of creams, oil-in-water or water-in-oil emulsions or multiple emulsions, sera, solutions, suspensions, gels, milks, lotions, sticks or even powders, and may be suitable for application to the skin, the lips and/or the integuments. These compositions comprise the excipients that are necessary for their formulation, such as solvents, emollients, thickeners, diluents, surfactants, antioxidants, bioactive agents, dyes, preserving agents and fragrances. They may be used as a skincare products and/or as skin makeup products.

The composition according to the invention may in particular consist of a haircare composition, and notably a shampoo, a hair conditioner, a treating lotion, a styling cream or gel, a hair restructuring lotion, a mask, etc. The cosmetic composition according to the invention may notably be used in treatments involving an application which may or may not be followed by rinsing, or alternatively in the form of a shampoo. The composition according to the invention may advantageously be used in antidandruff treatments. It may also be in the form of a dye or mascara to be applied with a brush or a comb, in particular to the eyelashes, the eyebrows or the hair.

The compositions according to the invention also comprise any additive commonly used in the envisioned field of application and also the adjuvants required for their formulation, such as solvents, thickeners, diluents, antioxidants, dyes, sunscreens, self-tanning agents, pigments, fillers, preserving agents, fragrances, odor absorbers, cosmetic or pharmaceutical active agents, essential oils, vitamins, essential fatty acids, surfactants, film-forming polymers, etc.

The INCI Dictionary & Handbook ("International Nomenclature of Cosmetic Ingredients" ($13^{th}$ edition, 2010) published by The Personal Care Products Council Inc., Washington, D.C.) describes a wide variety, without limitation, of cosmetic and pharmaceutical ingredients commonly used in the skincare industry, which are suitable for use as additional ingredients in the compositions according to the present invention.

In any case, a person skilled in the art will take care to ensure that these adjuvants and the proportions thereof are chosen such that the desired advantageous properties of the composition according to the invention are not adversely affected.

According to one advantageous embodiment of the invention, the amount of plant extract in the cosmetic composition according to the invention is from 0.002% to 20% by weight, and in particular from 0.01% to 10% by weight relative to the total weight of the composition.

According to another advantageous embodiment of the invention, the amount or content of plant extract in the nutricosmetic composition according to the invention is from 0.01% to 100% by weight relative to the total weight of the composition. More preferentially, the amount of plant extract is from 0.02% to 40% by weight and in particular from 0.2% to 20% by weight relative to the total weight of the composition.

A fourth subject of the invention is the cosmetic or nutricosmetic use of a composition according to the invention, for improving the appearance of the skin, mucous membranes or the integuments, for preventing and/or combating dryness of the skin and the mucous membranes, for preventing and/or combating the signs of aging and/or photoaging of the skin, for promoting bleaching of the skin and for promoting slimming.

Although the invention has been described in relation with several particular embodiments, it is quite obvious that it is not in any way limited thereto and that it encompasses all the technical equivalents of the means described and also combinations thereof if they fall within the context of the invention.

The use of the verb "contain", "comprise" or "include" and its conjugated forms does not exclude the presence of elements or steps other than those stated in a claim.

EXAMPLES

Example 1

Preparation of a Plant Extract According to the Invention from *Moringa Peregrina* Cake Seeds of *Moringa peregrina* (Forssk.) Fiori obtained when the fruit is ripe were dried to obtain an internal moisture content of less than 8% and preferentially about 6%, and then pressed with a mechanical endless screw press, so as to separate the oil from the rest of the seed in order to obtain, on the one hand, the virgin *peregrina* oil (INCI name: "*Moringa peregrina* seed oil") and, on the other hand, a cake. The cake is then isolated in the form of rolls precut into pieces of 1 to 2 cm on which the extraction is performed. The composition of the raw materials used in the process is given below.

TABLE 1

| Materials | Supplier | % | Real amount |
|---|---|---|---|
| Peregrina cake | | 8.4% | 33.6 |
| *precut into pieces of 1 to 2 cm | | | |
| Mains water | | 80.68% | 322.7 |
| Sodium hydroxide | Prochimia | 3.36% | 13.5 |
| Citric acid monohydrate F6000 | Adetis | 7.14% | 28.7 |
| Sodium benzoate | Adetis | 0.42% | 1.7 |
| Total | | 100 | 400.2 |

Protocol:
 a) A solution with a 1 molar concentration of a strong alkaline agent notably such as sodium hydroxide, potassium hydroxide or calcium hydroxide, or an aqueous mixture with a 1 molar concentration of strong alkaline agents, but preferentially sodium hydroxide, is prepared; this strong alkaline solution has a pH of greater than 13,
 b) Peregrina cake precut into pieces of about 1 cm is weighed out in a ratio [1:10] (mass/mass) in alkaline solution,
 c) the cake obtained in step b) is milled,
 d) the milled cake obtained in step c) is dispersed in aqueous phase,
 e) chemical proteolysis is performed on the aqueous dispersion obtained in step d), for a time of about 2 hours at a temperature of 20° C.,
 f) the proteolysis is neutralized, to stabilize the peptide hydrolyzate obtained, with a weak acid so as to buffer the solution in the 4.5-5.5 pH range,
 g) the peptide hydrolyzate is recovered by solid/liquid separation,
 h) the peptide hydrolyzate is purified by ultrafiltration.

A translucent yellow filtrate containing about 12.48% of dry matter is obtained. The liquid extract obtained is referred to hereinbelow as the "peregrina peptide hydrolyzate according to the invention" or "peregrina peptide hydrolyzate". This liquid extract is subsequently used for the efficiency tests.

This peregrina peptide hydrolyzate according to the invention has a density of greater than 1 and preferentially about 1.1, comprising a dry matter content of between 10% and 15%, preferentially about 12.5%, comprising between 1% and 6% of nitrogenous compounds, mainly peptides and glycopeptides, and also volatile nitrile derivatives in a proportion of from 0.5% to 1.5%, preferentially about 0.8%, and 20 mg/liter of polyphenols (0.0002%). The composition of the volatile compounds of the peregrina hydrolyzate according to the invention is given below.

TABLE 2

| Tr | CAS No. | Compounds | % DM |
|---|---|---|---|
| 4.42. | 64-17-5 | Ethanol | 0.809 |
| 5.58 | 67-64-1 | Acetone | 0.444 |
| 6.10 | 75-15-0 | Carbon disulfide | 0.327 |
| 7.83 | 78-93-3 | 2-Butanone | 0.165 |
| 8.57 | 141-78-6 | Ethyl acetate | 0.047 |
| 8.99 | 78-82-0 | Isobutyronitrile | 20.720 |
| 10.39 | 78-82-0 | Isobutyronitrile | 0.127 |
| 12.06 | 547-63-7 | Methyl isobutyrate | 0.201 |
| 14.10 | 18936-17-9 | 2-Methylbutanenitrile | 2.194 |
| 14.56 | 625-28-5 | 3-Methylbutanenitrile | 27.495 |
| 18.77 | 66-25-1 | Hexanal | 0.186 |
| 21.09 | 2253-73-8 | Isopropyl isothiocyanate | 4.590 |
| 23.65 | 628-73-9 | Hexanenitrile | 0.198 |
| 24.43 | 110-43-0 | 2-Heptanone | 0.093 |
| 27.18 | 4426-79-3 | 2-Isothiocyanatobutane | 1.058 |
| 27.59 | 80-56-8 | α-Pinene | 0.048 |
| 28.45 | 591-82-2 | Isobutyl isothiocyanate | 2.299 |
| 28.99 | 100-52-7 | Benzaldehyde | 1.753 |
| 29.77 | 108-95-2 | Phenol | 0.413 |
| 30.80 | 13475-82-6 | 2,2,4,6,6-Pentamethylheptane | 0.318 |
| 32.80 | 99-87-6 | para-Cymene | 0.232 |
| 33.10 | 138-86-3 | Limonene | 0.133 |
| 33.34 | 470-82-6 | Eucalyptol | 0.918 |
| 36.45 | 1195-32-0 | para-Cymenene | 0.035 |
| 36.88 | 124-19-6 | Nonanal | 0.080 |
| 40.26 | 65-85-0 | Benzoic acid | 19.150 |
| 41.07 | 1490-04-6 | Menthol | 0.918 |
| 56.29 | 96-76-4 | 2,4-Di-tert-butylphenol | 0.086 |
| | | Total | 85.035 |

The peregrina peptide hydrolyzate contains isopropyl isothiocyanate and isobutyl isothiocyanate in relatively high levels, confirming prior publications on the species (Kjaer et al. 1979, Isothiocyanates in Myrosinase-treated seed extracts of Moringa peregrina, Phytochemistry, 18, pages 1485-1487; AFSHARYPUOR et al., 2010, Volatile Constituents of the Seed Kernel and Leaf of Moringa peregrina (Forssk.) Fiori, Agricolt. Cultivated in Chabahar (Iran), Iranian Journal of Pharmaceutical Sciences 6(2): 141-144; Dehshahri S. et al., 2012, Determination of volatile glucosinate degradation products in seed coat, stem and in vitro cultures of Moringa peregrina (Forssk.) Fiori, ScienceOpen, Research in Pharmaceutical Sciences 7(1): 51-56). Isothiocyanates are compounds produced by various plants belonging to the order Brassicales, notably in the families Brassicaceae, Capparaceae, Caricaceae and Moringaceae as a defense system against attack by pathogens. In the genus Moringa, they have notably been identified in M. oleifera and M. stenopetala (Baker F.) Cufold. (ABD RANI N. Z., KHARAINA, H. and KUMOLOSASI, E., 2018, Moringa genus: A Review of Phytochemistry and Pharmacology, Frontiers in Pharmacology, volume 9, art. 108). Isothiocyanates are derived from the hydrolysis of glucosinolates by the enzyme myrosinase when plant tissues are damaged. It has been reported that isothiocyanates have various biological effects, such as antifungal activity (Troncoso-Rojas, R. and Tiznado-Hernández, M. E., 2007, Natural compounds to control fungal diseases in fruits & vegetables, in Troncoso-Rojas, R., Tiznado-Hernández, M. E., González-León, A. (eds) Recent advances in alternative postharvest technologies to control fungal diseases in fruits & vegetables. Editorial. Transworld Research Network, Kerala, India, pages 127-156; Troncoso-Rojas, R. et al., 2005, Analysis of the isothiocyanates present in cabbage leaves extract and their potential application to control Alternaria rot in bell peppers, Food Research International 38:701-708), antimicrobial, anticancer and antiinflammatory effects (Park, E. J. et al., 2011, Inhibition of lipopolysaccharide induced cyclooxygenase-2 expression and inducible nitric oxide synthase by 4-[(2'-O-acetyl-α-L-rhamnosyloxy)benzyl]isothiocyanate from M. oleifera, Nutrition and Cancer 63(6): 971-982; Rajan, T. S. et al., 2016, Anticancer activity of glucomoringin isothiocyanate in human malignant astrocytoma cells, Fitoterapa 110: 1-7; Padla E. P. et al., 2012, Antimicrobial isothiocyanates from the seeds of Moringa oleifera Lam, Zeitschrift für Naturforschung C, 67, 557-564; Waterman, C. et al., 2014, Stable, water extractable isothiocyanates from Moringa oleifera leaves attenuate inflammation in vitro. Phytochemistry 103: 114-122). Furfural is present in a very standard concentration found in this type of seed and in numerous dried fruits Carbon disulfide, isobutyronitrile, methyl isobutyrate, methylbutanenitrile and hexanenitrile are volatile compounds derived from amino acids. They are protein degradation markers. These degradation compounds represent about 50% of the volatile compounds in the extract of hydrolyzed *peregrina* cake. This result indicates that the extract is mainly constituted of proteins or peptides. Only very small traces of fats or free sugars were detected in the hydrolyzed extract of *Moringa peregrina*, and essential oils, the latter representing 4% of the volatile compounds with the presence of menthol at about 1%, the presence of eucalyptol at 1% and the presence of benzaldehyde at about 2%. In the dry matter, the citrate buffer (which is a saccharide compound) represents about 50% of the remainder and includes the glycosylated (saccharide) compounds resulting from the degradation by proteolysis of the proteins, oligopeptides and amino acids. Finally, the presence of about 20 mg/liter of polyphenols (0.0002%) derived from the *peregrina* seeds should be noted. The benzoic acid is not to be taken into consideration in the characterization since it is a stabilizer added to the extract. This liquid filtrate composes the extract according to the invention and is used in pure form in the tests that follow.

The dry matter of the extract described above is obtained via a gravimetric method based on the mass before and after evaporation present in the liquid extract. This dry mass is mainly composed of proteins and glycoproteins with a molecular weight of between 100 and 6000 Da, which are partially degraded and water-soluble, and are referred to as oligopeptides or glyco-oligopeptides or peptide hydrolyzate according to the invention, derived from the hydrolysis of *Moringa peregrina* cake. The dry extract also comprises a sodium citrate buffer which stabilizes these oligopeptides and glyco-oligopeptides in a static hydrolyzed state. Finally, this extract is microbiologically stabilized with a water-soluble preserving agent such as sodium benzoate.

Example 2

Effect of the *Peregrine* Peptide Hydrolyzate According to the Invention as an Antioxidant The object of this study is to evaluate the modulation of the antioxidant activity by the *peregrina* peptide hydrolyzate in an acellular in vitro colorimetric model using the DPPH (2,2-diphenyl-1-picrylhydrazyl) radical and also the reference antioxidant, ascorbic acid. The method used is known as inhibition. It is based on the degradation of the violet-colored oxidizing radical DPPH, which absorbs at 540 nm, with a reference antioxidant, ascorbic acid. This reaction serves as a positive control and leads to the formation of the DPPH compound which is colorless or even pale yellow. The *peregrina* peptide hydrolyzate according to the invention and the reference product "ascorbic acid" are placed in contact with the DPPH solution for 30 minutes at 40° C. The antioxidant activity is then evaluated by measuring the absorbance at 540 nm. The modulation of this activity is expressed as a percentage of stimulation of the antioxidant activity by the active agent tested, with, for reference, the maximum antioxidant activity obtained in the presence of ascorbic acid ($T_+$).

Protocol: A DPPH solution is incubated for 30 minutes at 40° C., in the absence (control) or in the presence of the *peregrina* peptide hydrolyzate according to the invention ($T_+$) and at decreasing concentrations of the test sample. At the end of the incubation period, the antioxidant activity in the presence of the reference product and in the presence or absence of the *peregrina* peptide hydrolyzate was revealed by staining after 30 minutes at 40° C. It was thus evaluated by measuring the absorbance of the reaction medium at 540 nm. For each concentration tested, the modulation of the antioxidant activity with the test product is calculated according to the following formula.

$$\text{Percentage modulation of antioxidant activity} = 100 \times [(OD_{540} \text{ Control} - OD_{540} \text{ Test product})/OD_{540} \text{ Reference product}]. \quad [\text{Math. 1}]$$

If the result is negative, the test product will be considered as oxidizing; if the result is positive, the percentage will be expressed as stimulation of the free-radical-scavenging activity. The results obtained for DPPH inhibition with the *peregrina* peptide hydrolyzate according to the invention are given below.

TABLE 3

|  |  | DPPH Inhibition |
|---|---|---|
| *Peregrina* peptide hydrolyzate according to the invention | 2% | 12 |
|  | 1.0% | 13 |
|  | 0.1% | 2 |

Conclusion: The *peregrina* peptide hydrolyzate according to the invention is capable of protecting against free radicals: it has significant antioxidant properties at and above a concentration of 1%.

Example 3

Effect of the *Peregrina* Extract According to the Invention as a Metalloprotease Inhibitor The object of this study is to evaluate the modulation of the anti-metalloprotease activity by the *peregrina* peptide hydrolyzate according to the invention in an in vitro acellular model using a type I collagenase and hyaluronidase, a substrate complex and a chromophore, ninhydrin. A buffered solution of type I collagenase and hyaluronidase reacts with a specific substrate complex and transforms it to form a compound that is capable of activating a chromophore by incubation at 80° C. for 15 minutes. The collagenase and hyaluronidase activities may thus be evaluated by measuring the absorbance at 565 nm. The sample is placed in contact with the collagenase and hyaluronidase solution together with the enzyme substrate complex at 37° C. for 5 minutes. The substrate transformed with the enzymes is capable of activating the chromophore by incubation at 80° C. for 15 minutes. The collagenase and hyaluronidase activities in the presence/absence of the sample are then evaluated by measuring the absorbance at 565 nm. The modulation of this activity is expressed as a percentage of inhibition or of activation of the collagenase and hyaluronidase activity in the absence of the active agent, i.e. only in the presence of the enzyme substrate.

Protocol: A solution of type I collagenase and hyaluronidase enzymes is incubated in its substrate for 5 minutes, in the absence or presence of the tested *peregrina* extract according to the invention. The solutions are then placed in contact with the chromogen ninhydrin, followed by incubating for 15 minutes at 80° C. At the end of the incubation period, the activity of the collagenase and hyaluronidase enzymes with and without the test or reference product was evaluated by measuring the absorbance of the reaction media at 565 nm. For each concentration tested, the modulation of the collagenase and hyaluronidase enzymatic activities with the test product is calculated according to the following formula.

$$\text{Percentage modulation of collagenase/hyaluronidase enzymatic activity} = 100 \times [(\text{OD test or reference product} - \text{OD collagenase/hyaluronidase alone})/\text{OD collagenase/hyaluronidase alone}]. \quad [\text{Math. 2}]$$

If the result is negative, the percentage is expressed as enzyme inhibition; if the result is positive, the percentage is expressed as enzyme activation. The results of the metalloprotease inhibition are given below.

TABLE 4

| | | Inhibition versus control (%) |
|---|---|---|
| Peregrina peptide hydrolyzate according to the invention | 1% | 100 |
| | 0.5% | 100 |
| | 0.1% | 92 |
| | 0.01% | 50 |

Conclusion: The *peregrina* peptide hydrolyzate according to the invention gives rise to strong inhibition of metalloproteases (collagenase/hyaluronidase). It is capable of totally inhibiting these metalloproteases at and above a concentration of 0.5% and has good potential for protecting the extracellular matrix of the skin with great efficiency and, via this inhibition, it reveals an antiaging effect.

Comparative tests are reported below with the extract obtained according to the Pierre Fabre patent FR 2 946 879, the results of which, according to the same test involving simply collagenase, are as follows

TABLE 5

| | Percentage | Inhibition versus control (%) |
|---|---|---|
| Extract of *Moringa oleifera* according to the Pierre Fabre patent | 1% | Concentration not compatible with the test system |
| | 0.5% | 4 |
| | 0.1% | 24 |
| | 0.01% | 42 |

Conclusion: the extract according to the Pierre Fabre patent shows a slight inverse-dose-dependent inhibitory action on collagenase activity with a peak inhibition of 42%, all concentrations combined, as opposed to a peak inhibition of 100% for the peptide hydrolyzate according to the invention.

The antiaging activity on this parameter appears to be different and novel in comparison with the effects observed with the extract according to the Pierre Fabre patent.

Example 4

Effect of the *Peregrina* Peptide Hydrolyzate According to the Invention on Inhibiting the Enzymes Histone Deacetylase (HDAC) and Sirtuin I The object of this study is to demonstrate the inhibitory activity of the *peregrina* peptide hydrolyzate according to the invention on the enzymes HDACs and sirtuin I. A buffered solution of HDACs & sirtuin I reacts with a substrate for 20 minutes at 37° C. and transforms it to form a compound which becomes stained in the presence of a developer after incubation at 37° C. for 10 minutes. The maximum deacetylation activity of sirtuins may thus be evaluated by measuring the absorbance at 405 nm. The *peregrina* extract according to the invention or the reference product "trichostatin A (STA) inhibitor 1 μM" are placed in contact with the solution of sirtuins together with the enzyme substrate for 20 minutes at 37° C., and the substrate transformed with the enzyme is stained by adding a developer. The deacetylating activity of the HDACs and sirtuin I in the presence of the active agent is then evaluated by measuring the absorbance at 405 nm. The modulation of this activity is expressed as a percentage of inhibition or activation of the maximum activity of the HDACs and of sirtuin I in the absence of the active agent, i.e. only in the presence of the substrate for the HDAC and sirtuin I enzymes.

Protocol: A solution of sirtuin enzymes is incubated in its substrate for 20 minutes in the absence (control) or presence of the reference product, or of increasing concentrations of the test products. The *peregrina* peptide hydrolyzate according to the invention is tested at the following concentrations: 2%; 1%; 0.1% (V/V). At the end of the incubation period, the activity of the sirtuin enzymes with and without the test or reference product was revealed by staining using a developer solution (10 minutes at 37° C.) and evaluated by measuring the absorbance of the reaction media at 405 nm. For each concentration tested, the modulation of the deacetylating activity of the histone deacetylase and sirtuin I enzymes with the test product is calculated according to the following formula.

$$\text{Percentage modulation of sirtuin enzymatic activity} = 100 \times [(\text{OD}_{405} \text{ test or reference product}) - (\text{OD}_{405} \text{ HDACs and sirtuin I alone})]/\text{OD}_{450} \text{ sirtuins alone.} \quad [\text{Math. 3}]$$

If the result is negative, the percentage is expressed as inhibition of the enzymatic reaction; if the result is positive, the percentage is expressed as activation of the enzymatic reaction. The results for the inhibition of the histone deacetylase (HDAC) enzymes are given below.

TABLE 6

| | Percentage | Inhibition versus control (%) |
|---|---|---|
| *Peregrina* peptide hydrolyzate according to the invention | 2% | 15 |
| | 1% | ns |
| | 0.10% | −18 |

Conclusion: At 2%, the *peregrina* peptide hydrolyzate according to the invention shows significant HDAC inhibition; this inhibition reflects the capacity for promoting the self-protection of skin cells against genetic drift, notably associated with the aging process. Thus the extract appears to be useful against one of the most common genetic drifts on the surface of the skin, namely fibrosis, which is manifested by the appearance of "skin tags" (fibrotic protuberances). The extract may advantageously interfere with fibrosis on the surface of the skin and thus prevent skin aging.

Example 5

Tensor Effect of the *Peregrina* Peptide Hydrolyzate According to the Invention

The object of this study is to evaluate the tensor effect of the active *peregrina* peptide hydrolyzate in an in vitro acellular model of lyophilized collagen discs. Lyophilized collagen discs 8 mm in diameter were used. The contraction of these discs in response to various treatments was measured by image analysis. The more the surface area of the collagen discs decreases, the greater the tensor effect of the active agents. The reference product used in this study is bovine serum albumin at 100 mg/ml.

Protocol: Collagen discs 8 mm in diameter were soaked with 40 µl of ultrapure water (control), the reference product, or increasing concentrations of the *peregrina* peptide hydrolyzate according to the invention: 0.05; 0.1 and 0.5% (v/v). The *peregrina* peptide hydrolyzate was dissolved directly in ultrapure water. Digital images of each of the discs were taken with a scanner before and 30 minutes after soaking. The surface area of the collagen discs was measured on the images using image analysis software. The results for the tensor effect are given below.

TABLE 7

|  |  | Reduction versus control (%) |
| --- | --- | --- |
| *Peregrina* peptide hydrolyzate according to the invention | 0.5% | 51.1 |
|  | 0.1% | 38.4 |
|  | 0.05% | ns |

Conclusion: The *peregrina* peptide nydroiyzate according to the invention snows a very significant tensor effect at low concentration (less than 1%). These results demonstrate a "lifting" effect and consequently a short-term antiaging effect.

Examples 2 to 5 demonstrate that the *peregrina* peptide hydrolyzate according to the invention has the profile of a good antiaging active agent, in the short or long term.

Example 6

Effect of the *Peregrina* Peptide Hydrolyzate According to the Invention on Inhibiting the Action of Endothelin-1

It has been reported in recent years that endothelin promotes an increase in intracellular calcium concentration in epidermal melanocytes (melanin cells) to facilitate cell growth via the intracellular signal transduction system. This action improves the activity of tyrosinase, which is a rate-determining enzyme in melanin synthesis (Kadono, S. et al., 2001, The Role of the Epidermal Endothelin Cascade in the Hyperpigmentation Mechanism of Lentigo Senilis, *Journal of Investigative Dermatology*, 116(4): 571-577). It has also been reported (Kawahara N. et al., 2005, About the Component of Snow Tea, *Collection of Pharmaceutical, Society of Japan annual convention Subject matter*, abstract 30-0823, page 159) that endothelin is a melanocyte activating factor produced by epidermal keratinocytes, and also an important factor in ultraviolet light-induced pigmentation or senile liver spots (Pang, Y., Geng, J., Qin, Y. et al. Endothelin-1 increases melanin synthesis in an established sheep skin melanocyte culture. *In Vitro Cellular & Developmental Biology—Animal* 52, 749-756 (2016) or Hachiya, Akira et al. Biochemical Characterization of Endothelin-converting Enzyme-1α in Cultured Skin-derived Cells and Its Postulated Role in the Stimulation of Melanogenesis in Human Epidermis. *Journal of Biological Chemistry*, volume 277, issue 7, 5395-540). These biological actions of endothelin suggest that active agents that are capable of inhibiting the action of endothelin may be useful for reducing or preventing melanin production or pigmentation.

Endothelin is the most potent vasoconstrictor known in the human body. Moreover, endothelin depletion is also known to create a vasodilatory effect (Hirata, Y. et al., 1988, Cellular mechanism of action by a novel vasoconstrictor endothelin in cultured rat vascular smooth muscle cells, *Biochemical and Biophysical Research Communications*, 154(3): 868-875; Shalinkumar P. et al., 2008, H2S Mediates the Vasodilator Effect of Endothelin-1 in the Cerebral Circulation. *American Journal of Physiology. Heart Circulatory Physiology*, 315, pages 1759-1764).

The object is to assay the type-1 endothelin in human microvascular endothelial cells after exposure for 24 hours to the *peregrina* peptide hydrolyzate according to the invention.

Protocol: Human microvascular endothelial cells were supplied by the company PELOBiotech and cultured in 96-well plates according to the supplier's production procedures. The extracts are left to act at various concentrations on the endothelial cells at 80% of confluence for 24 hours, and the endothelin-1 in the cell supernatants is then quantified using the PicoKine ELISA kit (EDN1). A viability test is performed beforehand to define the nontoxic doses to be used in the endothelin-1 assay. A negative control is performed using cells in culture medium without treatment. The positive control in the viability test is 0.5% SDS. All the conditions are prepared in culture media, and the cells are subsequently incubated at 36.5° C./5% $CO_2$ for 24 hours.

a) Application of the Test Solutions to the Endothelial Cells:

The test products are placed in contact with endothelial cells at subconfluence in 96-well plates. For each concentration, the test is performed on three wells. The plates are incubated for 24 hours±1 hour at 36.5° C./5% $CO_2$.

b) Viability Test:

The cell viability is evaluated with the MTT method on the cells after incubation with the products. After incubation for 24 hours, the supernatants are recovered and stored at −20° C. for the assays. The wells are then rinsed once with 200 µL of PBS. 50 µL of a 0.5 mg/ml MTT solution are added to each well: incubation for 3 hours at 36.5° C./5% $CO_2$. 100 µL of isopropanol are added to each well. After homogenization, an absorbance reading at 550 nm is taken. For each condition, the ratio of the mean optical density values of the cells to the mean optical density values of the negative controls determines the viability ratio.

c) Endothelin-1 Assay:

The assay is performed using the ELISA kit. The results for the inhibition of the action of endothelin are given below.

TABLE 8

|  | Extract concentration | Cell growth versus control (%) | Endothelin 1 versus control (%) | Endothelin 1 versus control (pg/ml) |
| --- | --- | --- | --- | --- |
| *Peregrina* extract according to the invention | 2% | +8.46 | −34.90 | −47.09 |
|  | 1% | 1.54 | −13.03 | −17.58 |
|  | 0.10% | −1.15 | −12.44 | −16.79 |

Conclusion: The viability test performed at the end of the treatment did not show any toxic effects for the concentrations tested.

The endothelin-1 assay is performed in the cell supernatants at nontoxic concentrations. The amount of endothelin-1 for each condition is assayed using the ELISA kit.

For the negative control cells, the values are of the order of 134.94 pg/ml. For the cells treated with various concentrations of extracts, the values are from 87.85 pg/ml (with 2% of the extract according to the invention) to 118.15 pg/ml (with 0.1% of the extract according to the invention), which shows very significant inhibitions at and above 0.1% of the extract according to the invention with about 12.44% inhibition of type-1 endothelin production and up to 34.90% inhibition with 2% of the extract according to the invention.

The results on endothelin and its specific dose-dependent inhibition demonstrate that the peptide hydrolyzate according to the invention is a powerful skin-lightening agent.

Example 7

Effect of the *Peregrina* Peptide Hydrolyzate According to the Invention on Releasing Free Fatty Acids Lipolysis in adipocytes, or the hydrolysis of triacylglycerol (TAG) to release fatty acids and glycerol for use by other organs, is a function unique to white adipose tissue. Lipolysis in adipocytes takes place on the surface of cytosolic lipid droplets, which have recently drawn much attention as dynamic organelles, an integral part of lipid metabolism. The recent identification of AdPLA as a main adipose phospholipase A(2) led to the discovery of a dominant autocrine/paracrine regulation of lipolysis by PGE (2). The above mechanisms are key factors in lipolysis and regulation thereof. Recent findings link lipolysis to genetic impairments or mutations and envisage the activation of lipolysis in adipocytes as a potential therapeutic target (Ahmadjan M. et al., 2010, Lipolysis in Adipocytes, *The International Journal of Biochemistry and Cell Biology*, 42(5): 555-559).

The object of the study is to evaluate the capacity of the peptide hydrolyzate according to the invention to increase glycerol release in human cell culture (adipocytes). The glycerol content is correlated with lipolysis. An increase in glycerol content implies a lipolytic effect. The cosmetic slimming effect is associated with the lipolytic effect.

Protocol: Human adipocytes are cultured in 24- and 12-well plates according to in-house procedures. For this, the samples are left to act at defined concentrations on confluent adipocytes for 24 hours. A preliminary viability test with MTT after 24 hours makes it possible to evaluate the cytotoxicity and to choose the concentrations for the "lipolytic effect" test. This "lipolytic effect" is evaluated by assaying the glycerol in the supernatants after 24 hours of exposure to the samples.

A negative control is performed using cells in culture medium without treatment. The positive control for the viability test is 0.5% SDS. The positive control for the "lipolytic effect" test is 0.05% caffeine. All the conditions are prepared in culture media, and the cells are subsequently incubated at 36.5° C./5% $CO_2$ for 24 hours±1 hour.

Application of the Test Solutions to the Adipocytes:
 The test products are placed in contact with the confluent adipocytes in 24-well plates (cytotoxicity test) and 12-well plates (test "lipolytic effect").
 For each concentration, the test is performed on three wells.
 The plates are incubated for 24 hours±1 hour at 36.5° C./5% $CO_2$.

Viability Test:
 The cell viability is evaluated with the MTT method on the cells after incubation for 24 hours with the products.
 After incubation for 24 hours, the intended wells are rinsed once with 200 µL of PBS.
 300 µl of a 0.5 mg/ml MTT solution are added to each well: incubation for 3 hours at 36.5° C./5% $CO_2$.
 800 µl of isopropanol are added to each well.
 After homogenization, an absorbance reading at 550 nm is taken.
 For each condition, the ratio of the mean optical density values of the cells to the mean optical density values of the negative controls determines the viability ratio.
 A viability cutoff value of 70% relative to the negative control value is used to classify the test substances as cytotoxic or noncytotoxic.

"Lipolytic Effect" Test:
 The lipolytic effect is evaluated by assaying the glycerol in the culture media after 24 hours±1 hour of incubation with the products.
 The culture media are mixed with the "free glycerol reagent" according to the supplier's protocol.
 The glycerol solution is used to make the standard range at concentrations of from 0 to 6250 µM.
 The OD reading is taken at 550 nm. The results for the free fatty acids release are given below.

TABLE 9

| | Concentration | Cell growth versus control (caffeine, %) | I Increase in glycerol production versus control (%) | Glycerol production (µM) |
|---|---|---|---|---|
| *Peregrina* peptide hydrolyzate | 2% | −6.16 | +40.00 | 8.32 |
| | 0.5% | −7 | +3.00 | 0.63 |
| | 0.10% | +9.03 | NS | 0 |

Conclusion: It has been shown that the peptide hydrolyzate according to the invention promoted the release of glycerol from human adipocytes and thereby induced a slimming effect.

Example 8

Effect of the *Peregrina* Extract According to the Invention on Stimulating the Protein ZAG Zinc α-2-glycoprotein (ZAG) is a plasmatic glycoprotein which draws its name from its electrophoretic mobility and its ability to be precipitated with Zn salts. ZAG is a member of the superfamily of immunoglobulin genes and has a three-dimensional structure that is highly homologous to the class I and II MHC molecules. ZAG has been detected immunohistochemically in normal secretory epithelial cells of the breast, prostate and liver, in the salivary, bronchial, gastrointestinal, and sweat glands, and in normal stratified epithelia, including the epidermis. ZAG mRNA remains uniformly distributed in various cell types [Za7]. Due to its production by the secretory epithelium, ZAG is present in the majority of the body secretions and constitutes 2.5% of the proteins in saliva and 30% of those in seminal fluids, respectively.

The standard functions of ZAG are unclear. However, ZAG has been isolated from the urine of human cancer patients suffering from cachexia and may function as a lipid-mobilizing factor. Purified ZAG extracted from human or murine serum, or extracted from human urine in cancer patients, induces lipolysis, leading to the release of glycerol. It also increases the use of lipids in human and murine adipocytes (Hirai K. et al., 1998, Biological Evaluation of a Lipid-Mobilizing Factor Isolated from the Urine of Cancer Patients, *Cancer Research*, 58(11): 2359-2365). ZAG activates guanosine triphosphate (GTP)-dependent adenylate cyclase activity on adipocyte membranes, increasing the cellular levels of cyclic adenosine monophosphate (cAMP). This may potentially lead to the activation of multiple cellular pathways.

To enhance the knowledge of the biological properties of ZAG, stable recombinant human (rh) ZAG transfectants were created in the B16F10 murine melanoma cell line. The effect of ZAG transfection on melanin production was determined in vitro and in vivo. Finally, the effect of ZAG on tyrosinase expression and activity was determined. As a whole, these studies show that ZAG inhibits melanin production in normal and malignant melanocytes. The mechanisms include post-transcriptional effects on the tyrosinase protein, with potential for additional indirect effects. These studies enabled the identification of a hitherto unknown biological function of ZAG and enabled a method for modulating melanin production, thus preventing and/or reducing skin and hair pigmentation due to the increased melanin production (Hale L., Method of Modulating Melanin Production, U.S. Pat. No. 7,803,750 B2, 2010) and (Ghada F. M. et al., 2015, Highlights in Pathogenesis of Vitiligo, *World Journal of Clinical Cases* 3(3): 221-230).

The object of this study is to evaluate the capacity of the peregrine peptide hydrolyzate according to the invention for increasing the release of ZAG in human cell culture (keratinocytes). The ZAG content is to be correlated with a bleaching effect, a slimming effect, an antifibrotic effect and a calmative effect.

Protocol: Normal human keratinocytes are isolated from foreskins and cultured in 24- and 96-well plates according to in-house procedures.

The samples are left to act at defined concentrations on the keratinocytes at 80% of confluence for 48 hours, and the ZAGs in the cell supernatants are then quantified using the ELISA kit.

A viability test is performed beforehand to define the nontoxic doses to be used in the ZAG assay.

The negative control is performed using cells in culture medium without treatment.

The positive control for the viability test is 0.5% SDS.

All the conditions are prepared in culture media, and the cells are subsequently incubated at 36.5° C./5% $CO_2$ for 24 hours for the viability test and 48 hours for the ZAG assay.
Application of Test Solutions to the Keratinocytes:
  The test products are placed in contact with the keratinocytes at subconfluence in 24- and 96-well plates.
  For each concentration, the test is performed on three wells.
  The plates are incubated for 24 hours and 48 hours at 36.5° C./5% $CO_2$.
Viability Test:
  The cell viability is evaluated with the MTT method on the cells after incubation with the products.
  After incubation for 24 and 48 hours, the intended wells are rinsed once with 200 µL of PBS.
  50 µl of a 0.5 mg/ml MTT solution are added to each well: incubation for 3 hours at 36.5° C./5% $CO_2$.
  100 µl of isopropanol are added to each well.
  After homogenization, an absorbance reading at 550 nm is taken.
  For each condition, the ratio of the mean optical density values of the cells to the mean optical density values of the negative controls determines the viability ratio.
ZAG Protein Assay:
  After incubation for 48 hours, all the supernatants are recovered and stored at −20° C. for the assays.
  The assay is performed using an ELISA kit. The results of the ZAG assay are given below.

TABLE 10

|  | Concentration | Cell growth versus control (%) | ZAG versus control (%) | ZAG versus control (ng/ml) |
|---|---|---|---|---|
| *Peregrina* peptide hydrolyzate | 2% | −17.88 | +337.80 | 0.390 |
|  | 1% | −12.54 | +195.73 | 0.157 |
|  | 0. | −3.88 | +151.83 | 0.085 |

Conclusion: *Peregrina* peptide hydolyzate may significantly increase ZAG production, with good dose dependency and low toxicity on human cells. As such, it has a bleaching effect, a slimming effect, an antifibrotic effect and a calmative effect based on its capacity for significantly increasing ZAG.

Example 9

Effect of the *Peregrina* Peptide Hydrolyzate According to the Invention on Inhibiting Melanin Production Skin pigmentation is a complex process which, both in the epidermis and in the hair follicles, commences with the synthesis of melanin in melanosomes inside the melanocytes, followed by transfer of the melanosomes to the surrounding keratinocytes, which in turn transport the pigment and optionally degrade it. In humans, the entire melanocyte population is located in the hair follicles and in the basal layer of the epidermis. Irrespective of their location in the skin, melanocytes have a common embryological origin, the neural crest from which they are derived in the form of melanoblasts (unpigmented cells). Two types of melanin exist in epidermal cells: eumelanin, a brown-black pigment, and pheomelanin, a yellow-red pigment. Eumelanosomes and pheomelanosomes coexist in melanocytes. Tyrosinase is the key enzyme which regulates the first steps in the synthesis of pheomelanin and eumelanin: the conversion of L-tyrosine into L-3,4-dihydroxyphenylalanine (L-DOPA) and the oxidation of this compound into dopaquinone. From dopaquinone, the synthetic pathways diverge for eumelanin and pheomelanin. The main role of melanin is to protect the skin against the harmful effects of UV radiation, thus preventing the development of skin cancer (Brenner M. et al., 2008, The protective role of melanin against UV damage in human skin, *Photochemistry and Photobiology* 84(3): 539-549).

The object is to collate all the data used, and also the results obtained, in order to perform the melanin modulation test on human melanocytes after exposure to the *peregrina* extract according to the invention for 5 days.

Protocol: Human melanocytes are cultured in 96- and 24-well plates.

The *peregrina* extract according to the invention is allowed to act on the confluent melanocytes at concentrations of 5%, 2%, 1% and 0.1% for 5 days. A pretest of viability with MTT after 24 hours makes it possible to evaluate the cytotoxicity and to choose the concentrations for the melanin modulation test. This modulation is evaluated by assaying the melanin in the cell lyzates after 5 days of exposure to the extracts. The negative control is performed using cells in culture medium without treatment. The positive control for the viability test is 0.5% SDS. For the melanin modulation test, media with and without α-MSH are used as negative controls.

All the conditions are prepared in culture media, and the cells are subsequently incubated at 36.5° C./5% $CO_2$ for 24 hours for the cytotoxicity test and 5 days for the melanin assay.

a) Application of the test solutions to the melanocytes: The test concentrations are placed in contact with the confluent melanocytes in 96-well plates (cytotoxicity test) and 24-well plates (melanin assay). For each concentration, the test is performed on three wells. The plates are incubated for 24 hours ±1 hour and 5 days at 36.5° C./5% $CO_2$.

b) Viability test: The cell viability is evaluated with the MTT method on the cells after incubation for 24 hours with the products. After incubation for 24 hours, the intended wells are rinsed once with 200 μL of PBS. 50 μl of a 0.5 mg/ml MTT solution are added to each well and incubation is performed for 3 hours at 36.5° C./5% $CO_2$. 150 μl of isopropanol are added to each well. After homogenization, an absorbance reading at 550 nm is taken. For each condition, the ratio of the mean optical density values of the cells to the mean optical density values of the negative controls determines the viability ratio.

A viability cutoff value of 70% relative to the negative control value is used to classify the test substances as cytotoxic or noncytotoxic. A "noncytotoxic" classification is given on the in vitro results for a viability >70% and a "cytotoxic" classification is given for a viability ≤70%.

The 5% concentration of the extract according to the invention proved to be cytotoxic at 5% under the test conditions. The 2%, 1% and 0.1% concentrations are thus used for the melanin modulation test. The amount of melanin present in the cells is assayed after cell lysis. The results for the inhibition of melanin production are given below.

TABLE 11

| | Extract concentration | Cell growth versus control (%) | Melanin inhibition versus control (%) | Melanin content (μg/ml) |
|---|---|---|---|---|
| Peptide hydrolyzate according to the invention | 2% | −24.48 | +16.50 | 152 |
| | 1.0% | −17.15 | +55.00 | 82 |
| | 0.10% | −18.06 | +71.40 | 52 |

Conclusion: The *peregrina* peptide hydrolyzate according to the invention inhibits melanin production in cellulo, which gives it a depigmenting effect and a skin bleaching property.

Example 10

Effect of the *Peregrina* Peptide Hydrolyzate According to the Invention on Modulation of the DKK1 and DKK3 Assay The involvement of interactions between melanocytes and fibroblasts in melanogenesis regulation is well known and has been intensively studied. Although these interactions are not yet fully understood, they are the cause of the "whiteness" of the palmoplantar areas and are now used in cosmetics for the development of depigmenting products. Yamaguchi et coll. (Yamaguchi Y. et al., 2004, Mesenchymal-Epithelial Interactions in the Skin: Increased Expression of Dickkopf by Palmoplantar Fibroblasts Inhibits Melanocyte Growth and Differentiation, *Journal of Cell Biology* 165(2): 275-285) demonstrated that a soluble messenger produced by the fibroblasts of the palmoplantar regions was capable of modifying the differentiation program of the melanocytes of these regions, leading to a decrease in melanin production. This messenger was identified by the team as a protein named Dikkopf-1 (DKK-1).

The signaling pathways used by DKK-1 to produce these results are now clearly identified. By virtue of its antagonistic action on the Wnt receptor, DKK-1 is in fact capable of "shunting" the intracellular signaling pathways activated by β-catenin, which are generally responsible for regulation of the genes involved in melanogenesis. Yamaguchi et coll. also demonstrated that DKK-3, a molecule similar to DKK-1, but without any effect on the Wnt receptor, might play a regulatory role on the effect of DKK-1. Indeed, the greater the amount of DKK-3 in the vicinity of this Wnt receptor, the weaker the interactions between DKK-1 and this receptor. Increasing DKK3 reduces the inhibitory effects of DKK-1 on melanogenesis. The studies by Yamaguchi et coll. (cf. supra) suggest that the identification of agents which have an influence on the DKK1/DKK3 ratio in normal human dermal fibroblast cultures of non-palmoplantar origin would make it possible to control melanin production using normal human non-palmoplantar melanocytes The object of this study is to evaluate the effect of the compound known as "*peregrina* peptide hydrolyzate" on DKK-1 synthesis and release in a model composed of normal human fibroblasts in monolayer culture.

Protocol: Human fibroblast cells were obtained from a 68-year-old donor. To perform the experiments, the fibroblasts were grown as a monolayer culture until confluence was reached. 100 nM dexamethasone was used as a reference inducer of DKK-1 synthesis and release.

Skin discs were incubated for 48 hours in the absence (control) or presence of reference product or test product: *Peregrina* peptide hydrolyzate: 0.01%; 0.1% and 0.5% (v/v).

At the end of the incubation, the incubation media were removed to perform the DKK-1 release measurement.

The test compound "*peregrina* peptide hydrolyzate" was diluted directly in the incubation medium so as to reach the various concentrations described above.

At the end of the 48-hour incubation period, the DKK-1 released into the incubation media was quantified by means of a specific sensitive ELISA kit.

At the end of the incubation period, the proteins contained in the cell lyzates were quantified by means of a spectro-colorimetric method (Bradford method).

The results are expressed as ng DKK-1 per mg of protein (mean±S.D.).

The significance level between the "control" and the "reference product" was evaluated by means of a Student's test (*: p<0.05).

The significance level between the "control" and the "test product" was evaluated by a one-way analysis of variance (one-way ANOVA) followed by a Holm-Sidak test (*: p<0.05).

Under our experimental conditions, the reference product known as "dexamethasone", tested at 100 nm, significantly increased the released DKK-1 by 181.8% (p<0.01) relative to the "control". The results regarding the modulation of the DKK1 assay are given below.

TABLE 12

|  | Concentration | Cell growth versus control (%) | DKK1 versus control (%) |
| --- | --- | --- | --- |
| *Peregrina* peptide hydrolyzate | 0.5% | +1.9 | +131.50 |
|  | 0.1% | 0 | +32.30 |
|  | 0.05% | −0.6 | +26.10 |

Study on UKK3

The object of this study is to evaluate the effect of compounds known as "*peregrina* peptide hydrolyzate" on the synthesis and release of DKK-3 in a model composed of normal human fibroblasts in monolayer culture.

Human fibroblast cells were obtained from a 68-year-old donor.

To perform the experiments, the fibroblasts were grown as a monolayer until confluence was reached.

Human fibroblast cells were obtained from a 68-year-old donor.

To perform the experiments, the fibroblasts were grown as a monolayer until confluence was reached.

At the end of the 48-hour incubation period, the DKK-3 released into the incubation media was quantified by means of a specific sensitive ELISA kit.

At the end of the incubation period, the proteins contained in the cell lyzates were quantified by means of a spectrocolorimetric method (Bradford method).

The results are expressed as ng DKK-3 per mg of protein (mean±S.D.).

The significance level between the "control" and the "reference product" was evaluated by means of a Student's test (*: p<0.05).

The significance level between the "control" and the "test product" was evaluated by a one-way analysis of variance (one-way ANOVA) followed by a Holm-Sidak test (*: p<0.05). The results regarding the modulation of the DKK3 assay are given below.

TABLE 13

|  | Concentration | Cell growth versus control (%) | DKK3 versus control (%) |
| --- | --- | --- | --- |
| *Peregrina* peptide hydrolyzate | 0.5% | 101.9 | −20.7 |
|  | 0.1% | env. 100 | −8 |
|  | 0.05% | 99.4 | −3.9 |

Conclusion: The *peregrina* peptide hydrolyzate according to the invention can considerably increase the production of DKK1, and tends to reduce the production of DKK3 in the human cells. It has a high capacity to decrease skin pigmentation by means of the principle of palmoplantar inhibition, via its ability to considerably increase DKK1 and significantly decrease DKK3, thus increasing the DKK1/DKK3 ratio. The increase in this ratio has the effect of limiting the pre-melanocyte/melanocyte differentiation pathway; thus, the number of operational melanocytes decreases over time, reducing the skin's ability to become colored.

Example 11

Effect of the *Peregrina* Peptide Hydrolyzate According to the Invention on Preserving DNA The dynamics of telomere lengths are very important for regulating the replicative lifespan in cells, in particular in the case of species that re long-lived. Telomere shortening and telomerase activity are important factors in aging and tumorigenesis (Shay, J. W., 2005, Senescence and Immortalization: Role of Telomeres and Telomerase, Carcinogenesis 26(5): 867-874). Telomeres are complex nucleotide sequences which cap the ends of chromosomes from degradation, undesirable fusion-recombination, and inappropriate activation of the DNA damage response. They also play an essential role in cell division and chromosome stability. There is ever-increasing evidence that the stability of telomeres may be affected by occupational and environmental exposures, since some of these factors have been associated with an increase in inflammation, oxidative stress, DNA damage, chromosomal aberrations and epigenetic alterations. Extremely short and long telomeres have been associated with neurodegenerative diseases, cardiovascular diseases (CVD) and cancer risk.

Telomerase is a ribonucleoprotein which catalyzes the addition of telomeric repeats to the ends of telomeres. Telomeres are long sections of repeat sequences that cap the ends of chromosomes and have the role of stabilizing the chromosome. In humans, telomeres are generally 7 to 10 kb long and comprise several repeats of the sequence -TTAGGG-.

Telomerase is not expressed in the majority of adult cells and the length of telomeres decreases with successive replication cycles. After a certain number of replication cycles, the progressive shortening of the telomeres causes cells to enter a telomere crisis phase, which in turn leads to cellular senescence. Certain diseases are associated with rapid telomere loss, resulting in premature cellular senescence. Expression of the gene coding for the human telomerase protein in human cells (Blasco M., 2007, Telomere Length, Stem Cells and Aging, *Nature Chemical Biology* 3, pages 640-649) has been demonstrated to impart an immortal phenotype, probably by circumventing the natural senescence pathway of the cells. Furthermore, expression of the telomerase gene in aging cells with short telomeres has been demonstrated to produce an increase in telomere length and to restore a phenotype that is generally associated with younger cells.

The object of this study is to evaluate the effect of the compound known as "*peregrina* peptide hydrolyzate" on telomere shortening in a model composed of normal human fibroblasts in monolayer culture. It is well known that the telomere corresponds to a biological clock. The length of telomeres gradually decreases with cell divisions, ultimately leading to the inability of the cell to undergo replication. Measurement of telomere length was performed by means of quantitative PCR and comparison with telomere length between cells at passages 2 and 5.

Protocol: Human fibroblast cells were obtained from a 44-year-old donor. To perform the experiments, cells were used at passage 2 and 5. The fibroblasts were cultured for three consecutive passages in the absence (control) or presence of an increasing test concentration of the *peregrina* peptide hydrolyzate: 0.01%; 0.1% and 0.5% (v/v).

Preparation of the test compound: The test compound "*peregrina* peptide hydrolyzate" was diluted directly in the incubation medium so as to reach the various concentrations described above.

At the end of the incubation, the cells were trypsinized. The DNA was extracted from the cells by means of a dedicated DNA extraction kit. The DNA was quantified by NanoDrop.

The telomere length was measured by quantitative PCR (q-PCR). For each sample, the variation in the telomere length was measured by relative quantification using the SCR (single copy reference) gene as the reference gene. For each sample, a q-PCR is performed using a set of telomere primers that recognizes and amplifies the telomere sequences and a second q-PCR is performed using the set of SCR primers that recognizes and amplifies a 100-bp region on human chromosome 17 and serves as a reference for data normalization.

The results are expressed in relative units corresponding to the length of the telomeres relative to the cells at passage 2 (mean±S.D.). The significance level between "control" at passages 2 and 5 was evaluated by means of a Student's t test (*$p<0.05$). The significance level between "control" and "test compound" was evaluated independently for each product by a one-way analysis of variance (one-way ANOVA) followed by a Holm-Sidak test (*: $p<0.05$).

Results: Under our experimental conditions, the *peregrina* peptide hydrolyzate tested at 0.05%, 0.1% and 0.5% (v/v) significantly decreased the telomere shortening in normal human fibroblasts.

Telomere shortening: inhibition (in comparison with the control) at 0.05% (v/v)+8.9% ($p<0.05$) and at 0.1% (v/v)+15.1% ($p<0.01$) and at 0.5% (v/v)+16.6% ($p<0.01$).

TABLE 14

|  | Concentration | Cell growth versus control (%) | Telomere length versus control (%) |
|---|---|---|---|
| *Peregrina* peptide hydrolyzate | 0.5% | +1.9 | +16.60 |
|  | 0.1% | ca. 0 | +15.10 |
|  | 0.05% | −0.6 | +8.90 |

Conclusion: In a context of normal multiplication or division of human cells, the *peregrina* peptide hydrolyzate according to the invention demonstrates a capacity for significantly increasing the telomere length. Telomeres are the caps involved in the protection of DNA material; increasing the size of the telomeres preserves the integrity of the DNA material over time. Increasing the telomere length is correlated with the ability to preserve DNA material. Since the *peregrina* peptide hydrolyzate can increase this length, it is thus involved in the preservation of human genetic material (DNA).

Example 12

Comparative Tests of Various Products on Moisturization of the Skin's Surface

Corneometry study enables measurement of the moisturizing effect of a product on the skin's surface. The machine used is a corneometer equipped with a probe which notably measures the moisture of the skin by impedancemetry. A panel composed of six people (two men and four women) tested under similar conditions of hydrometry and temperature on the inner faces of their forearms. The inner face of the left forearm bears zones 1 and 2, and the inner face of the right forearm bears zones 3 and 4.

Zone 1 corresponds to the zone of application of the reference moisturizing gel; zone 2 corresponds to the zone of application of the reference gel+2% of the peptide hydrolyzate according to the invention; zone 3 corresponds to the zone of application of the reference gel+2% of the peptide hydrolyzate with *Moringa oleifera*; zone 4 corresponds to the zone of application of the reference gel +2% of Purisoft® according to patent FR 3 076 460 from BASF Beauty Care Solutions.

The amount of product applied to each zone is the same, and the measurement times are the same for each of the zones. A first value is taken before applying the product to each zone so as to determine the zero moisture state of the skin. Next, for each zone and each product, a first measurement is taken 5 minutes after applying the product to the zone, always by the same operator. To conclude, a final measurement is taken 30 minutes after the second measurement above, again by the same operator.

The combination of the differences observed before and after application does not follow a normal law studied in ANOVA (analysis of variance). The value obtained by the difference between the before and after measurements is thus the parameter studied. The results obtained constitute a qualitative rather than a quantitative trend of the values obtained:

TABLE 15

| Zone | Mean of the estimated differences |
|---|---|
| 1 = reference (placebo) | 1.286 |
| 2 = ref. + peptide hydrolyzate according to the invention 2% | 1.190 |
| 3 = ref. + *M. oleifera* peptide hydrolyzate 2% | −0.214 |
| 4 = ref. + BASF Purisoft ® extract 2% | −0.667 |

Conclusion: Zone 2 shows a positive skin moisturizing value between before and after application of the product containing the extract according to the invention, whereas zones 3 and 4 containing the *Moringa oleifera* extracts according to 2 extraction modes, show negative values, i.e. the skin is less moisturized after application of the products than it was before. The peptide hydrolyzate according to the invention makes it possible to maintain the benefit of moisturization in a topical application product, which distinguishes the *peregrina* peptide hydrolyzate according to the invention from the other extracts tested. FIG. 1 shows the results obtained.

Example 13

Makeup Product Formulation

TABLE 16

| Ingredients | % |
| --- | --- |
| Water | qs |
| Caprylic/capric triglyceride | 19.0000 |
| *Acacia Senegal* gum | 7.0000 |
| Charcoal | 6.0000 |
| Glycerol | 5.0000 |
| Propanediol | 5.0000 |
| Bentonite | 3.1500 |
| Cetearyl glucoside | 3.0000 |
| Cetearyl alcohol | 3.0000 |
| Benzyl alcohol | 1.0000 |
| *Peregrina* peptide hydrolyzate according to the invention | 2.0000 |
| Cellulose gum | 0.8000 |
| Xanthan gum | 0.1750 |
| Citric acid | 0.1750 |

Example 14

Washing Product Formulation

TABLE 17

| Ingredients | % |
| --- | --- |
| Water | qs |
| Sodium cocoyl sulfate | 5.0000 |
| Sodium cocoyl isethionate | 4.0000 |
| Bentonite | 3.7800 |
| Caprylic/Capric triglyceride | 2.0000 |
| *Peregrina* peptide hydrolyzate according to the invention | 1.0000 |
| Gluconolactone | 0.7500 |
| Sodium benzoate | 0.5450 |
| Fragrance | 0.5000 |
| Xanthan gum | 0.2700 |
| Sodium stearoyl glutamate | 0.2250 |
| Citric acid | 0.2250 |
| Calcium gluconate | 0.0050 |

Example 15

Care Product Formulation

TABLE 18

| Ingredient | % |
| --- | --- |
| Water | qs |
| Caprylic/Capric triglyceride | 18.0000 |
| Bentonite | 4.2000 |
| Cetearyl alcohol | 1.5000 |
| *Peregrina* peptide hydrolyzate according to the invention | 2.0000 |
| Gluconolactone | 0.7500 |
| Sodium benzoate | 0.5450 |
| Xanthan gum | 0.5000 |
| Fragrance | 0.5000 |
| Sodium stearoyl glutamate | 0.2500 |
| Citric acid | 0.2500 |
| Calcium gluconate | 0.0050 |

Example 16 relaxing or slimming tablet of 1 g: 2% dry extract according to the invention (containing 60% peptide hydrolyzate on an inulin support)+47% calcium carbonate containing 200 IU vitamin D+25% magnesium gluconate+23% inulin+3% magnesium stearate).

Example 17

Slimming powder in a 750 mg gel capsule containing 200 mg of caffeine, 200 mg of dry extract according to the invention (containing 60% of peptide hydrolyzate on an inulin support), 200 mg of chitosan and 150 mg of calcium carbonate.)

Example 18

Appetite suppressant & slimming powder in a 750 mg gel capsule containing 200 mg of caffeine, 200 mg of dry extract according to the invention (containing 60% of peptide hydrolyzate on an inulin support), 200 mg of chitosan and 150 mg of konjac (glucomannan).

Example 19

Sublingual relaxant spray containing 2% extract according to example 1. 1% *Rhodiola* mother tincture, 1% lemon balm mother tincture, 1% valerian mother tincture, 1% hawthorn mother tincture, 2% horsetail extract, 0.15% salicylic acid, 7% sorbitol, and qs water.

Example 20

Antiwrinkle Cream Containing 2% Hydrolyzed Extract According to Example 1

TABLE 19

| Ingredients | % | INCI |
| --- | --- | --- |
| Water | 70.95 | Aqua |
| Salicylic acid | 0.15 | Salicylic acid |
| Sodium benzoate | 0.5 | Sodium benzoate |
| Frametime CXG | 3.2 | Bentonite & xanthan gum & sodium stearoyl glutamate & citric acid |
| Xanthan gum FF | 0.2 | Xanthan gum |
| Plant glycerol - Palmera G995E | 3.5 | Glycerol |
| 50/50 Cetylstearyl alcohol | 1 | Cetearyl alcohol |
| DUB MCT 5545 | 18 | Caprylic/capric triglyceride |
| Plumeria fragrance DIV/02356 | 0.5 | Fragrance |
| Extract of hydrolyzed peregrina | 2 | *Moringa peregrina* hydrolyzed seed extract |

Example 21

Toxicological Tests of the Hydrolyzate According to the Invention

Preparation of the peptide hydrolyzate in accordance with example 1: Unshelled seeds of *Moringa peregrina* (Forssk.) Fiori harvested when the fruit is ripe were dried to obtain an internal moisture content of less than 8% and preferentially about 6%, and then pressed with a mechanical endless screw press, so as to separate the oil from the rest of the seed in order to obtain, on the one hand, the virgin oil and, on the other hand, a cake. The cake is then isolated in the form of precut rolls in pieces of 1 to 2 cm. By following the protocol described in example 1, the liquid extract is obtained, which is used in pure form in the following tests.

1. Determination of the Mutagenic Activity on the Bacterial Strain *Salmonella typhimurium* (TA 100)—Bacterial Reverse Mutation Test The test was conducted in three main phases:
- A preliminary experiment is performed in order to evaluate the cytotoxicity of the element to be tested and to select the dose range for the subsequent experiments,
- A first genotoxicity experiment (Test 1), with and without metabolic activation, with direct incorporation of the test system and the test (or of the controls) on minimal agar, on the dose range defined by the preliminary study,
- A second experiment (Test 2), with preincubation of the test system and of the test element (or of the controls), with and without metabolic activation, with dose levels defined by the study director after analysis of the results of the first experiment. This second experiment was performed in order to confirm or complete the results of the first one, in particular when equivocal or negative results were obtained.

Dilutions of the extract according to example 1 were prepared in water to perform the cytotoxicity test.

Said test was performed on the strain *Salmonella typhimurium* TA100 at concentrations of 5000, 1600, 500, 160 and 50 µg/plate, with and without S9-Mix.

The reagents used for preparing the 59-Mix were prepared according to the following instructions:

TABLE 20

| | Final concentration |
|---|---|
| MgCl$_2$ (0.4M) + KCl (1.65M) | 8 mM + 33 mM |
| Glucose 6-phosphate (0.2M) | 5 mM |
| NADP (0.1M) | 4 mM |
| Phosphate buffer for S9-Mix (pH 7.4 - 0.2M) | 0.1M |
| S9 fraction | 10% |
| Water | Adjust to final concentration |

The bacteria were exposed to the test extract with and without the metabolic activation system. The metabolic system used is a cofactor-supplemented post-mitochondrial fraction (S9). This S9 fraction, a microsomal fraction of Sprague-Dawley rat liver homogenate treated with an enzyme inducer, is prepared according to Maxon, D. M. and Ames, B. N. (1983) and was supplied by Moltox™, It is stored at a temperature below −70° C. The S9 microsomal fraction was used at a concentration of 10% in S9-Mix. The protocol applied was as follows:

The following were introduced into three hemolysis tubes:
assay without metabolic activation:
0.1 ml of the various concentrations of the test elements.
0.5 ml of sterile 0.2 M, pH 7.4 phosphate buffer,
2 ml of top agar for *S. typhimurium,*
0.1 ml of bacterial inoculum (TA100).
assay with metabolic activation:
0.1 ml of the various concentrations of the test elements,
2 ml of top agar for *S. typhimurium,*
0.1 ml of bacterial inoculum (TA100),
0.5 ml of S9-Mix.

Mix and pour onto the surface of the bottom agar previously spread in Petri dishes.
Incubate at 37° C.±2° C. for 48 to 72 hours.
These assays were performed for each test: preliminary cytotoxicity test, test 1 and test 2. The untreated control, the negative controls and the positive controls produced during the preincubation method were incubated for 20 to 30 minutes at 37° C.±2° C. before pouring the top agar.

The protocol applied was as follows:
Introduce the following into four 2-ml fractions of top agar for *S. typhimurium:*
0.1 ml of 0.2 M, pH 7.4 phosphate buffer,
0.1 ml of solvent,
0,1 ml of S9-Mix,
0.1 ml of the preparation of the test element at the highest concentration,
A 2 ml fraction of top agar for *S. typhimurium* is used to check its sterility.
Mix and pour onto the surface of the bottom agar previously spread in Petri dishes.
Incubate at 37° C.±2° C. for 48 to 72 hours.
The test is performed in triplicate.
No bacterial growth should be observed.
For at least five concentrations of the test extract, a test without metabolic activation and a test with metabolic activation were performed.

Expressing and Interpreting the Results

Many criteria make it possible to determine whether a result is positive, notably an increase in the number of revertants correlated to the dose of the test item, or a reproducible increase in the number of revertants at one or more concentrations, with or without metabolic activation.

The test element is considered to be mutagenic if, on conclusion of the verification steps, a dose-effect relationship was reproducibly obtained on one or more of the five strains with and/or without metabolic activation. Mutagenicity is only considered for a given concentration when the number of revertants is at least equal to twice the rate of spontaneous reversion for the strains TA98, TA100 and TA102 (R≥2) and three times the rate of spontaneous reversion for the strains TA1535 and TA1537 (R≥3).

The test element is considered to be non-mutagenic if, on conclusion of test 1 and test 2, the frequency of revertants always remained less than twice the rate of spontaneous reversion for all concentrations of the test element, for the strains TA98, TA100, and TA102 (R<2) and less than three times the rate of spontaneous reversion for the strains TA1535 and TA1537 (R<3), with and without metabolic activation, and provided that it was checked that the absence of the mutagenic effect was not related to the toxicity of the concentrations tested.

The preliminary study showed no cytotoxicity of the test element; consequently, this concentration range was used for the genotoxicity test 1.

On the basis of the result obtained for test 1, it was decided to use the same dilution range for test 2. The analysis of the revertants shows that:
No cytotoxic effect was observed,
No concentration of the test extract showed a ratio R greater than or equal to at least twice the rate of spontaneous reversion for TA98, TA100, and TA102 or three times the rate of spontaneous reversion for TA1535 and TA1537, with and without metabolic activation, No dose response was observed, irrespective of the test system or of the test conditions.

In the light of the results obtained in this study, the peptide hydrolyzate according to example 1 may be considered as having no mutagenic or promutagenic activity.

2. In Vitro Phototoxicity Test 3T3 NRU

The principle of the test is based on comparison of the cytotoxicity of the peptide hydrolyzate according to example 1 in the presence and absence of a non-cytotoxic dose of UVA, on cells in culture. The cytotoxicity is evaluated by determining cell viability using a vital stain: neutral red, 24 hours after treatment with the reference elements and the extract of *M. peregrina* according to the invention with or without UVA irradiation. The cells used are mouse embryo fibroblasts of the Balb/c 3T3 clone 31 line (ATCC-CCL163). The positive control is a chlorpromazine solution (CAS No.: 69-09-0). The negative control is a diluent for the test extract and for the reference (buffered saline solution±1% solvent). The peptide hydrolyzate was tested at eight concentrations in at least four culture wells per concentration studied, in the presence or absence of UVA. The fibroblasts were trypsinized, and two 96-well culture plates were seeded with 100 µl of a cell suspension containing $2\times10^5$ cells/ml (i.e., $2\times10^6$ cells per well) in complete culture medium.

The seeded plates were incubated for 24 hours at 37° C. and 5% $CO_2$. At the end of the incubation, semi-confluence of the cell lawn was checked. The dilutions were prepared just before being deposited on the cells. The pH of the highest concentration was measured; it was between 6.5 and 7.8. The culture medium was removed, each well was prerinsed cautiously with 150 µl of PBS maintained at room temperature and then treated with 100 µl of each extract or reference dilution. The culture plates were incubated in the dark for 1 h±5 min at 37° C. and 5% $CO_2$. Irradiation was performed using a Bio Sun solar irradiator (Vilber Lourmat RMX3W). The Bio Sun machine is a system which controls the UV irradiation by means of a programmable microprocessor. The system continuously follows the UV light emission. The irradiation stops automatically when the energy delivered is equal to the programmed energy. The spectral irradiance of the test device was measured in the wavelength range from 250 to 700 nanometers with a calibrated spectroradiometer.

One of the two plates was irradiated with its cover on at room temperature, and the other plate was protected from UVA and was maintained at room temperature during the irradiation. After irradiation, the treatment medium was aspirated and the cells were rinsed. 100 µl of complete culture medium were then added cautiously and the plates were incubated for 18 to 22 h at 37° C. and 5% $CO_2$. The next day, the cell viability (growth, morphology, monolayer integrity) was evaluated by observations using a phase-contrast microscope. The culture medium was removed, and each well was prerinsed and maintained at room temperature before being treated with 100 µl of the staining solution. The plates were returned to the incubator for 3 hours under the same conditions. The staining solution was removed and the cells were rinsed, the rinsing solution was then removed and 150 µl of desorption solution were added to each well. The plates were shaken until the crystals were fully dissolved. The absorbance values were measured at 450 nm.

Test Validation:

The UVA sensitivity of the cells is checked approximately every 10 passages by evaluation of their viability after exposing them to increasing irradiation doses. The cells are cultured at the density used in the test. They are irradiated the next day at a dose of 2.5 and 9 $J/cm^2$ and the cell viability is determined one day later by means of the NRU test. The cells meet the quality criteria if their viability after irradiation at 5 $J/cm^2$ of UVA is greater than or equal to 80% of the viability of the controls kept in the dark; at the highest dose of 9 $J/cm^2$ of UVA, the viability must be at least equal to 50% of that of the controls kept in the dark.

Results:

The negative control has an absorbance of greater than or equal to 0.4. Chlorpromazine, the positive control, has an $IC_{50}$ value of between 0.1 and 2 µg/ml in the presence of UVA and between 7 and 90 µg/ml in the absence of UVA. These results make it possible to validate the test. The concentration of the peptide hydrolyzate of *peregrina* cake giving 50% cell death in the presence or absence of UVA cannot be estimated. The mortality never reached 50%. The concentration of the peptide hydrolyzate of *peregrina* cake giving 50% cell viability in the presence or absence of UVA cannot be estimated. The viability is always greater than 50%.

Conclusion: Under the experimental conditions adopted, the peptide hydrolyzate of *peregrina* cake may be considered as non-phototoxic.

3. Evaluation of the Ocular Irritant Potential by Study of the In Vitro Cytotoxicity Using the Neutral Red Release Method on the SIRC Cell Line This in vitro study is based on evaluation of the cytotoxicity of the peptide hydrolyzate of *peregrina* cake by determining the concentration which results in 50% cell death ($IC_{50}$) on a cell monolayer by means of the neutral red release technique. The cells used are mycoplasma-free SIRC rabbit corneal fibroblasts (ATCC-CCL60).

The peptide hydrolyzate was diluted to 25% and 50% in physiological saline. The fibroblasts were trypsinized and two 24-well culture plates were seeded at a rate of 1 ml of a cell suspension containing $2\times10^5$ cells/ml in complete culture medium. The seeded plates were incubated overnight at 37° C. and 5% $CO_2$. At the end of the incubation, the confluence of the cell lawn was checked. The staining solution was prepared at 0.5 mg/ml in complete culture medium. The culture medium was removed; 1 ml of the staining solution was placed in each well. The plates were returned to the incubator at 37° C. and 5% $CO_2$ for 3 hours±15 minutes. After this contact time, the staining solution was removed and replaced with 1 ml of complete culture medium per well. The plates were maintained at room temperature for at least 30 minutes in order to stabilize the system before contact with the extract or the reference. Each well was rinsed with 2 ml of PBS, maintained at room temperature, and 500 µl of each dilution of peptide hydrolyzate or of reference were then placed in contact with the cell lawn. The contact time was 60 seconds (30 seconds for the positive control). The treatment was performed well by well with the stopwatch started at the moment that the peptide hydrolyzate or the reference was deposited. The plate was shaken manually throughout the treatment. After 55 seconds (or 25 seconds for the positive control), the dilution was aspirated. At precisely 60 or 30 seconds, five successive rinses were performed ($5\times2$ ml PBS maintained at room temperature). The supernatant was aspirated after each rinse and after the final rinse the wells remained free of medium while awaiting the revelation phase. After complete treatment of the culture plate, 1 ml of the desorption solution was deposited in each well. The plate was shaken for about 15 minutes until homogeneous staining was obtained. The solutions obtained for each culture well were taken up and divided into two wells of a 96-well plate, i.e. 150 µl/well.

Results:

The concentration of the peptide hydrolyzate leading to 50% cell death was evaluated as >50%. The percentage of cell death at 50% of peptide hydrolyzate was evaluated as 17%.

Conclusion: Under the experimental conditions adopted, the cytotoxicity of the peptide hydrolyzate of *peregrina* cake may be considered as being of negligible cytotoxicity, 4. Evaluation of the Skin Compatibility of a Peptide Hydrolyzate after a Single Application Under an Occlusive Dressing for 48 Hours Under Dermatological Control The aim of this study is to evaluate the degree of skin compatibility of the peptide hydrolyzate by epicutaneous test, performed on the antero-external face of the arm for 48 hours; and in general to evaluate the capacity of the peptide hydrolyzate to keep the skin in good condition. 10 healthy female or male volunteers, from 18 to 65 years old, having neither dry skin nor sensitive skin and free of any dermatological lesions on the treatment area were to be included in the study. The skin compatibility of the peptide hydrolyzate, prepared in the form of a lotion containing 5% of the *peregrina* extract according to example 1 and 95% of a propanediol/sorbitol mixture, was evaluated 48 hours after the initial application between 30 and 40 minutes after removing the dressing. The skin reactions (erythema and edema) were scored from 0 to 3 according to the following scales:

TABLE 21

| Score | Erythema (Er) | Edema (Ed) |
|---|---|---|
| 0 | no erythema | no edema |
| 0.5 | Barely perceptible erythema, very slightly pink coloring on part of the patched zone | palpable, barely perceptible edema |
| 1 | Mild erythema, pinkish coloring over the entire patched area | palpable and visible edema |
| 2 | Moderate erythema, clear coloring over the entire patched area | clear edema with or without papules or vesicles |
| 3 | Pronounced erythema, intense coloring over the entire patched zone | pronounced edema spreading outside the patched zone, with or without papules or vesicles |

Any other skin reactions (bullae, papules, vesicles, dryness, desquamation, roughness, soap effect, etc.) were evaluated according to the following scale and reported descriptively:

0: no reaction
0.5: very mild
1: mild
2: moderate
3: pronounced

At the end of the study, a mean irritation score (M.I.S.) was calculated according to the following formula:

$$M.I.S.=\text{Sum of skin reactions }(Er+Oe+\text{bullae+papules+vesicles})/\text{Number of volunteers analyzed} \quad [\text{Math. 4}]$$

The M.I.S. obtained made it possible to classify the test extract according to the scale presented in the table below:

| M.I.S. ≤ 0.20 | Non-irritant |
|---|---|
| 0.20 < M.I.S. ≤ 0.50 | Slightly irritant |
| 0.50 < M.I.S. ≤ 2 | Moderately irritant |
| 2 < M.I.S. ≤ 3 | Highly irritant |

Results: The Mean Irritation Score (M.I.S.) for the peptide hydrolyzate of *peregrina* cake is equal to: 0.

Conclusion: The peptide hydrolyzate of *peregrina* cake may be considered as non-irritant after 48 consecutive hours of application on 12 volunteers.

General Conclusion of the Tests:

The results of the tests performed above are conclusive and demonstrate, for the peptide hydrolyzate according to example 1:

1) the eye and skin irritation tests are negative
2) the phototoxicity tests are negative
3) the mutagenicity tests are negative.

The safety of the peptide hydrolyzate according to the invention is demonstrated and ideal for large-scale topical cosmetic use without restriction as regards the target population.

Example 22

Skin-Depigmenting Activity of the Hydrolyzed Cake Extract

The aim of the test is to evaluate the depigmenting potential and the acceptability of a cosmetic product according to the invention after 28 days of application. The test product is the antiwrinkle cream described in example 20.

Population Analyzed:

Number of volunteers included and analyzed: 23

Females with an average age of 64 years, between 44 and 70 years old, with lentigos on the face, neck, neckline and/or hands.

Procedure adopted for the study: twice a day, for 28 days, apply a pea-sized amount of product to the clean skin of the face, neck, neckline and hands and massage in until the product has completely penetrated; avoid contact with the eyes; apply the antisun product provided before any exposure to sunlight.

Evaluation Criteria:

Evaluation of depigmenting potential: mexametric measurements at three sites (treated pigmented zone, treated unpigmented zone, untreated unpigmented control zone), on D1 and D28.

Feedback from the volunteers regarding the discomfort sensations.

Photographs for illustrative purposes of a lentigo with the C-Cube videodermoscope (Pixience SAS, Toulouse, France) on D1 and D28 (transmitted in the form of contact sheets by WeTransfer when the final report was made available).

Cosmetic acceptability: questionnaire filled in by the volunteer on D28.

Study Results:

TABLE 22

| | Melanin index (A.U.) | | | | | |
|---|---|---|---|---|---|---|
| | Pigmented treated zone | | Unpigmented treated zone | | Unpigmented untreated zone | |
| | D 1 | D 28 | D 1 | D 28 | D 1 | D 28 |
| Mean | 200.9 | 183.8 | 143.5 | 133.8 | 122.9 | 121.4 |
| Standard deviation | 42.8 | 35.3 | 27.2 | 22.7 | 33.4 | 32.7 |
| Median | 185.0 | 180.5 | 149.5 | 131.0 | 116.0 | 117.5 |
| Minimum | 126.0 | 116.5 | 95.5 | 91.5 | 79.0 | 84.5 |
| Maximum | 289.5 | 251.5 | 197.0 | 173.5 | 228.0 | 214.5 |
| % of variation | −8.5% | | −6.8% | | −1.2% | |

TABLE 22-continued

| | Melanin index (A.U.) | | | | | |
|---|---|---|---|---|---|---|
| | Pigmented treated zone | | Unpigmented treated zone | | Unpigmented untreated zone | |
| | D 1 | D 28 | D 1 | D 28 | D 1 | D 28 |
| Value of p* | 0.000 | | 0.001 | | 0.148 | |
| Significance** | S | | S | | NS | |

*Wilcoxon test for paired data;
**S: Significant (p ≤ 0.05) NS: Not Significant (p > 0.05)

The analysis of the mexametric measurements revealed a statistically significant decrease in the melanin index on the two treated zones (pigmented and unpigmented areas) on D28 relative to D1. The variations recorded between D28 and D1 in the untreated zone were found to be statistically insignificant.

Conclusion: Under the conditions of the study, the test product showed significant depigmenting efficacy after 28 days of use.

The invention claimed is:

1. An extract of *Moringa peregrina* seed cake comprising a peptide hydrolyzate which comprises amino acid derivatives, amino acids, peptides and glycopeptides with a molecular weight of between 100 Da and 6000 Da obtained by ultrafiltration with a cutoff threshold between 100 Da and 6000 Da, and characterized in that the extract is obtained from a seed cake of unshelled seeds of ripe *Moringa peregrina* fruit, by chemical proteolysis at a pH of greater than 13 for a time of about 2 hours at a temperature of between 16 and 25° C.

2. The extract as claimed in claim 1, the extract further comprising between 0.3% and 3% of volatile compounds, of which 50% of the volatile compounds is constituted of light nitrile compounds, of which 5% to 10% of the light nitrile compounds is constituted of isothiocyanate derivatives, of which 1% to 5% of the isothiocyanate derivatives is constituted of essential oil.

3. The extract as claimed in claim 1, wherein said extract is a dried extract and comprises the peptide hydrolyzate in an amount greater than 10% by weight of dry matter of peptides, oligopeptides, glycopeptides and amino acids or volatile nitrile derivatives thereof.

4. The extract as claimed in claim 1, wherein the extract is obtained by:
 a) collecting and drying the unshelled seeds, harvested when the fruit of *Moringa peregrina* is ripe, to obtain an internal moisture content of less than 8%,
 b) pressing the dried seeds so as to separate the oil from the rest of the seed, so as to obtain the seed cake comprising less than 6% by weight of residual oil,
 c) milling the seed cake obtained in step b),
 d) dispersing the milled cake obtained in step c) in aqueous phase,
 e) performing said chemical proteolysis of the aqueous dispersion obtained in step d) for a time of about 2 hours, at a pH of greater than 13 and at a temperature of between 16 and 25° C.,
 f) neutralizing the proteolysis to stabilize the peptide hydrolyzate obtained,
 g) recovering the peptide hydrolyzate by solid/liquid separation,
 h) purifying the peptide hydrolyzate by ultrafiltration with a cutoff threshold between 100 Da and 6000 Da.

5. A cosmetic or nutricosmetic composition comprising an effective amount of the extract of *Moringa peregrina* seed cake of claim 1, and a physiologically acceptable excipient.

6. The composition as claimed in claim 5, wherein a cosmetic composition formulated for topical application to the skin and in that the extract of *Moringa peregrina* seed cake is present in the composition in a concentration of from 0.002% to 20% by weight relative to the total weight of the composition.

7. The composition as claimed in claim 5, wherein a nutricosmetic composition formulated for ingestion and in that the extract of *Moringa peregrina* seed cake is present in the composition in a concentration of from 0.01% to 100% by weight relative to the total weight of the composition.

8. The composition as claimed in claim 5, for one or more of the following uses: improving the appearance of the skin, mucous membranes or the integuments, preventing and/or combating dryness of the skin and the mucous membranes, preventing and/or combating the signs of aging and/or photoaging of the skin, promoting bleaching of the skin and promoting slimming.

9. A process for obtaining an extract of *Moringa peregrina* seed cake as claimed in claim 1, comprising the following steps:
 a) collecting and drying the unshelled seeds, harvested when the fruit of *Moringa peregrina* is ripe to obtain an internal moisture content of less than 8%,
 b) pressing the dried seeds so as to separate the oil form the rest of the seed, so as to obtain the cake comprising less than 6% by weight of residual oil,
 c) milling the case obtained in step b),
 d) dispersing the milled cake obtained in step c) in aqueous phase,
 e) performing chemical proteolysis of the aqueous dispersion obtained in step d) for a time of about 2 hours, at a pH of greater than 13 and at a temperature of between 16 and 25° C.,
 f) neutralizing the proteolysis to stabilize the peptide hydrolyzate obtained,
 g) recovering the peptide hydrolyzate by solid/liquid separation,
 h) purifying the peptide hydrolyzate by ultrafiltration with a cutoff threshold between 100 Da and 6000 Da and then, optionally,
 i) performing lyophilization of the peptide hydrolyzate obtained in step h).

10. The process as claimed in claim 9, wherein the solid/liquid separation of step g) is performed by centrifugation, dewatering or filtration.

* * * * *